United States Patent
Abe et al.

(10) Patent No.: US 11,236,334 B2
(45) Date of Patent: Feb. 1, 2022

(54) MODIFIED POLYNUCLEOTIDE

(71) Applicant: National University Corporation Nagoya University, Nagoya (JP)

(72) Inventors: Hiroshi Abe, Nagoya (JP); Zhaoma Shu, Nagoya (JP)

(73) Assignee: NATIONAL UNIVERSITY CORPORATION NAGOYA UNIVERSITY, Nagoya (JP)

( * ) Notice: Subject to any disclaimer, the term of this patent is extended or adjusted under 35 U.S.C. 154(b) by 0 days.

(21) Appl. No.: 16/640,213

(22) PCT Filed: Aug. 17, 2018

(86) PCT No.: PCT/JP2018/030549
§ 371 (c)(1),
(2) Date: Feb. 19, 2020

(87) PCT Pub. No.: WO2019/039403
PCT Pub. Date: Feb. 28, 2019

(65) Prior Publication Data
US 2020/0362338 A1 Nov. 19, 2020

(30) Foreign Application Priority Data

Aug. 22, 2017 (JP) .............................. JP2017-159770

(51) Int. Cl.
*C12N 15/113* (2010.01)
*A61K 31/7088* (2006.01)

(52) U.S. Cl.
CPC ........ *C12N 15/113* (2013.01); *A61K 31/7088* (2013.01)

(58) Field of Classification Search
CPC .............. C12N 15/113; C12N 2310/11; C12N 2310/14
See application file for complete search history.

(56) References Cited

U.S. PATENT DOCUMENTS

| 6,399,589 | B1 * | 6/2002 | Gosselin | ................ | C07H 19/10 514/45 |
| 2014/0142253 | A1 | 5/2014 | Srivastava et al. | | |
| 2015/0158964 | A1 * | 6/2015 | Morvan | ................ | C07H 21/04 525/54.2 |
| 2015/0168341 | A1 * | 6/2015 | Tayebi | ................ | C23C 16/00 204/403.01 |
| 2015/0232957 | A1 * | 8/2015 | Fournier-Wirth | ...... | C07H 21/00 435/5 |
| 2019/0111152 | A1 * | 4/2019 | Hartwich | ....... | C12Y 301/03001 |

FOREIGN PATENT DOCUMENTS

| JP | H05-505941 | A | 9/1993 | | |
| JP | 2002511885 | A | 4/2002 | | |
| JP | 2002529439 | A | 9/2002 | | |
| JP | 2004331574 | A | 11/2004 | | |
| JP | 2009543783 | A | 12/2009 | | |
| JP | 2010521133 | A | 6/2010 | | |
| JP | 2016507484 | A | 3/2016 | | |
| JP | 2016509575 | A | 3/2016 | | |
| WO | 9114696 | A1 | 10/1991 | | |
| WO | 9905302 | A1 | 2/1999 | | |
| WO | 0027795 | A1 | 5/2000 | | |
| WO | 2008008476 | A2 | 1/2008 | | |
| WO | 2008022309 | A2 | 2/2008 | | |
| WO | WO-2008141799 | A1 * | 11/2008 | ............ | C07F 9/6561 |
| WO | 2013/126034 | A1 | 8/2013 | | |
| WO | 2014088920 | A1 | 4/2014 | | |
| WO | 2014088923 | A1 | 6/2014 | | |
| WO | 2015/145417 | A1 | 10/2015 | | |
| WO | WO-2015188197 | A2 * | 12/2015 | ............ | C07H 19/10 |
| WO | 2017/029664 | A1 | 2/2017 | | |
| WO | WO-2017083637 | A1 * | 5/2017 | .......... | C07F 9/65512 |
| WO | 2019/008574 | A1 | 1/2019 | | |

OTHER PUBLICATIONS

Azema et al. Bioorganic & Medicinal Chemistry Letters 16, 3440-3443 (Year: 2006).*
Asseline et al. Tetrahedron Letters vol. 30, 2521-2524 (Year: 1989).*
Liepold et al. Anal Bioanal Chem 391: 1759-1772 (Year: 2008).*
Phares et al. Anal. Chem 81, 1095-1100 (Year: 2009).*
Tanaka, Hiromu et al., "Synthesis of oligo-nucleic acid coupled to membrane-permeable molecules", Abstracts (CD-ROM) of the spring annual conference of the Chemical Society of Japan, vol. 98, 2D5-45, Mar. 6, 2018, pp. 1-2.
Shu, Zhaotna et al., "Development of membranepermeable oligo-nucleic acid", Abstracts (CD-ROM) of the annual conference of the Pharmaceutical Socieityof Japan, vol. 138, 28M-ptn15s, Mar. 5, 2018, p. 119.
English translation of International Search Report issued in corresponding International Application No. PCT/JP2018/030549 dated Sep. 25, 2018, pp. 1-4.
Office Action dated May 10, 2021 for corresponding EP application No. 18848251.7, 6 pages.
Mallikaratchy et al., "Using aptamers evolved from cell-SELEX to engineer a molecular delivery platform", Chemical Communications, 2009, No. 21, pp. 3056-3058.
Glen Research Corporation, "Thiol-Modifier S-S Phosphoramidite and Supports", 2012, 2 pages.
Semenyuk et al., "A base-stable dithiomethyl linker for solid-phase synthesis of oligonucleotides", Tetraheoron Letters, 2007, vol. 48, No. 3, pp. 469-472.

(Continued)

*Primary Examiner* — Brian Whiteman
(74) *Attorney, Agent, or Firm* — MH2 Technology Law Group, LLP

(57) ABSTRACT

The present invention addresses the problem of providing a technique for more conveniently delivering a polynucleotide in a less cytotoxic form into a cell. This problem is solved by a polynucleotide modified by a molecule that contains a structure that contains a disulfide bond and/or a thiol group.

11 Claims, 8 Drawing Sheets

Specification includes a Sequence Listing.

(56) References Cited

OTHER PUBLICATIONS

Liepold et al., "Electrically detected displacement assay (EDDA): a practical approach to nucleic acid testing in finical or medical diagnosis", Analytical and Bioanalytical Chemistry, 2008, vol. 3 91, No. 5, pp. 1759-1772.
Supplementary European Search Report dated Aug. 26, 2021 for corresponding European Patent Application No. 18848251.7, 19 pages.
Johnson et al., "A Label-Free, Electrochemical SERS-Based Assay for Detection of DNA Hybridization and Discrimination of Mutations", Journal of the American Chemistry Society, 2012, vol. 134, No. 34, pp. 14099-14107.

\* cited by examiner

MODIFIED POLYNUCLEOTIDE

CROSS-REFERENCE TO RELATED APPLICATIONS

This application is a U.S. National Stage application of PCT/JP2018/030549 filed 17 Aug. 2018, which claims priority to Japanese Application No. 2017-159770 filed 22 Aug. 2017, the entire disclosures of which are incorporated herein by reference.

SEQUENCE LISTING

The present application contains a Sequence Listing which has been submitted electronically in ASCII format and is hereby incorporated by reference in its entirety. Said ASCII copy, created on 18 Feb. 2020, is named P18-160_Sequence_Listing.txt and is 2 Kilobytes in size.

TECHNICAL FIELD

The present invention relates to a modified polynucleotide and the like.

BACKGROUND ART

The development of art for the delivery into cells of polynucleotides, e.g., siRNA, and the induction of the expression of their functionality is progressing in, for example, the drug sector. Polynucleotides are negatively charged due to the presence of the phosphate group, and as a result they exhibit a low efficiency of penetration across the cell membrane, which is also negatively charged. Due to this, when a polynucleotide is to be delivered into a cell, the efficiency of delivery has been raised by complexing the polynucleotide with a cationic lipid and delivering this into the cell (PTL 1).

However, the use of a cationic lipid requires a procedure in which it is complexed with the polynucleotide prior to delivery into the cell. Cationic lipids are also known to exhibit cytotoxicity.

CITATION LIST

Patent Literature

PTL 1: Japanese Translation of PCT Application No. 2002-529439

SUMMARY OF INVENTION

Technical Problem

The present invention addresses the problem of providing a technique for more conveniently delivering a polynucleotide in a less cytotoxic form into a cell. The present invention preferably also addresses the problem of providing a technique for more efficiently delivering a polynucleotide into a cell.

Solution to Problem

As a result of intensive investigations in view of the aforementioned problem, the present inventors discovered that a polynucleotide modified by a molecule that contains a structure that contains a disulfide bond and/or a thiol group, is more efficiently delivered into the cell through the simple addition of the modified polynucleotide to the cell culture medium and without requiring a complicated procedure such as formation of a complex with a cationic lipid. It was also discovered that this modified polynucleotide exhibits a lower cytotoxicity. The present inventors continued their investigations based on this knowledge and achieved the present invention.

That is, the present invention encompasses the following embodiments.

Item 1. A modified polynucleotide modified by a molecule that contains a structure represented by general formula (1):

[Chem. 1]

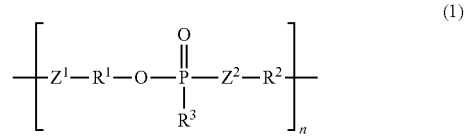

wherein, $R^1$ and $R^2$ are identical or different and represent a single bond or a divalent group optionally containing at least one group selected from the group consisting of —S—S— and —SH; $R^3$ represents —O— or —O—$R^{31}$, wherein $R^{31}$ represents a monovalent group optionally containing at least one group selected from the group consisting of —S—S— and —SH; $Z^1$ and $Z^2$ are identical or different and represent —O— or —NH—; provided that at least one of $R^1$, $R^2$, and $R^3$ contains at least one group selected from the group consisting of —S—S— and —SH; and n represents any integer.

Item 2. The modified polynucleotide according to item 1, wherein $R^1$ is an alkylene group or a group derived from a ring having —S—S— in a structure of the ring, $R^2$ is a single bond, and $R^3$ is —O— or —O—$R^{31a}$—S—S—$R^{31b}$, wherein $R^{31a}$ represents an alkylene group or —$R^{311a}$—NH—COO—$R^{312a}$—, wherein $R^{311a}$ and $R^{312a}$ are identical or different and represent an alkylene group; and $R^{31b}$ represents a protecting group.

Item 3. The modified polynucleotide according to item 1 or 2, wherein (A) $R^1$ is an alkylene group, $R^2$ is a single bond, and $R^3$ is —O—$R^{31a}$—S—S—$R^{31b}$, wherein $R^{31a}$ represents an alkylene group or —$R^{311a}$—NH—COO—$R^{312a}$—, wherein $R^{311a}$ and $R^{312a}$ are identical or different and represent an alkylene group; and $R^{31b}$ represents a protecting group, or (B) $R^1$ is a group derived from a ring having a group represented by —S—S— in a structure of the ring, $R^2$ is a single bond, and $R^3$ is —O⁻.

Item 4. The modified polynucleotide according to any of items 1 to 3, wherein (A1) $R^1$ is an alkylene group having 3 to 6 carbon atoms, $R^2$ is a single bond, and $R^3$ is —O—$R^{31a}$—S—S—$R^{31b}$, wherein $R^{31a}$ represents an alkylene group having 3 to 6 carbon atoms or —$R^{311a}$—NH—COO—$R^{312a}$—, wherein $R^{311ba}$ and $R^{312a}$ are identical or different and represent an alkylene group having 2 to 6 carbon atoms; and $R^{31b}$ represents an alkyl group or aryl group, or (B1) $R^1$ is a group derived from a 4- to 8-membered ring having a group represented by —S—S— in a structure of the ring, $R^2$ is a single bond, and $R^3$ is —O⁻.

Item 5. The modified polynucleotide according to any of items 1 to 4, wherein n is 1 to 30.

Item 6. The modified polynucleotide according to any of items 1 to 5, wherein both $Z^1$ and $Z^2$ are —O—.

Item 7. The modified polynucleotide according to any of items 1 to 6, wherein the polynucleotide is a polynucleotide for delivery into a cell.

Item 8. The modified polynucleotide according to any of items 1 to 7, wherein the polynucleotide is at least one selected from the group consisting of antisense polynucleotides, siRNA, miRNA, miRNA precursors, aptamers, guide RNA, mRNA, noncoding RNA, DNA, and unnatural nucleic acids (LNA, PNA, and morpholine nucleic acids).

Item 9. The modified polynucleotide according to any of items 1 to 8, wherein a nucleotide length of the polynucleotide is a nucleotide length of not more than 200.

Item 10. The modified polynucleotide according to any of items 1 to 9, wherein the structure represented by general formula (1) is linked to a terminal of the polynucleotide.

Item 11. The modified polynucleotide according to any of items 1 to 10, wherein the structure represented by general formula (1) is linked to a 5' terminal of the polynucleotide.

Item 12. A delivery agent for delivering the modified polynucleotide according to any of items 1 to 11 into a cell, the delivery agent containing the modified polynucleotide.

Item 13. A pharmaceutical containing the modified polynucleotide according to any of items 1 to 11.

Item 14. A reagent containing the modified polynucleotide according to any of items 1 to 11.

Item 15. A molecule for modifying a polynucleotide, the molecule containing a structure represented by general formula (1):

[Chem. 2]

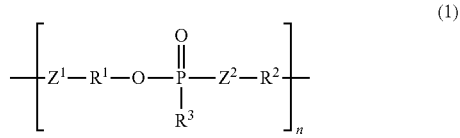

(1)

wherein, $R^1$ and $R^2$ are identical or different and represent a single bond or a divalent group optionally containing at least one group selected from the group consisting of —S—S— and —SH; $R^3$ represents —O$^-$ or —O—$R^{31}$, wherein $R^{31}$ represents a monovalent group optionally containing at least one group selected from the group consisting of —S—S— and —SH; $Z^1$ and $Z^2$ are identical or different and represent —O— or —NH—; provided that at least one of $R^1$, $R^2$, and $R^3$ contains at least one group selected from the group consisting of —S—S— and —SH; and n represents any integer.

Advantageous Effects of Invention

The present invention can thus, through the use of a polynucleotide modified by a molecule that contains a structure that contains a disulfide bond and/or a thiol group, provide a technique for more conveniently delivering a polynucleotide in a less cytotoxic form into a cell. A preferred embodiment of the present invention enables a polynucleotide to be delivered into a cell more efficiently than in the conventional art of using a cationic lipid.

DESCRIPTION OF EMBODIMENTS

Figure 1:
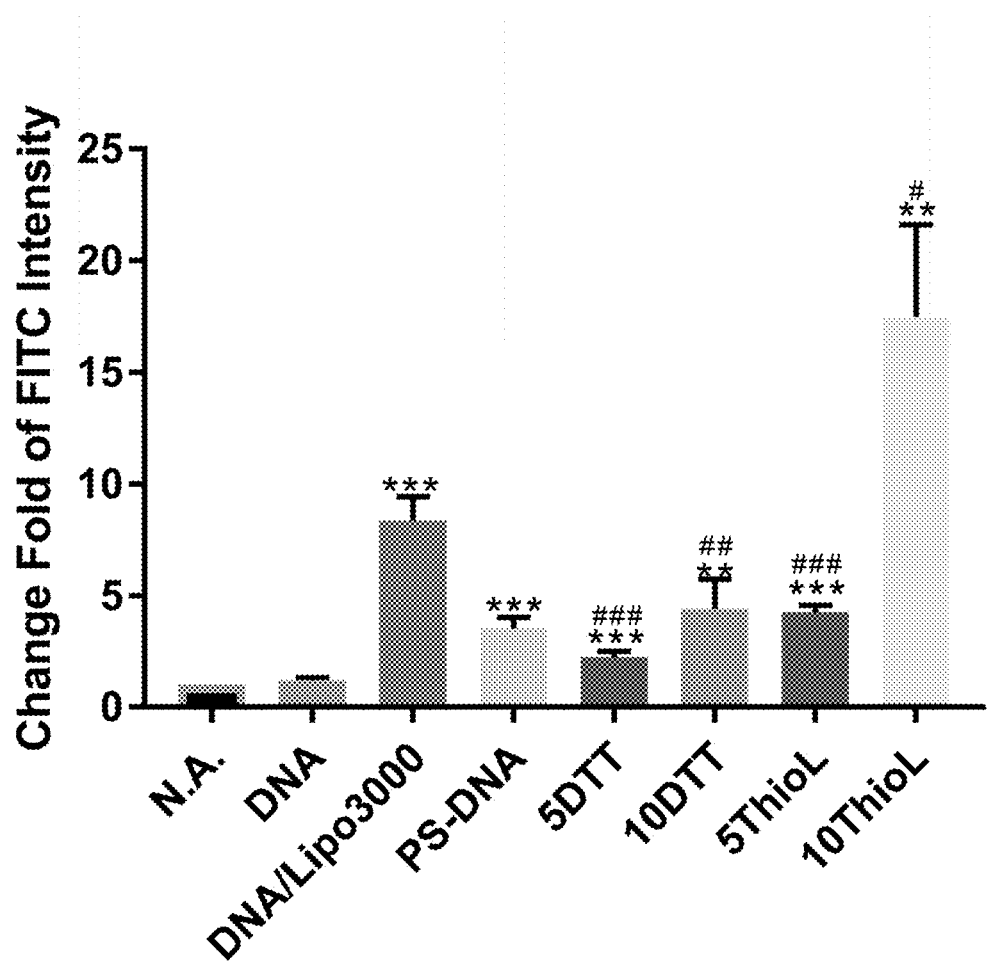
FIG. 1 gives the results of the cell membrane permeability test of Test Example 1, where the horizontal axis gives the case of no addition of polynucleotide to the culture medium as "N.A.", the cases of the addition to the culture medium of the polynucleotide of Examples or Comparative Examples as such (DNA (Comparative Example 1), PS-DNA (Comparative Example 3), 5DTT (Example 1), 10DTT (Example 2), 5ThioL (Example 3), 10ThioL (Example 4)), and the case of the addition to the culture medium of the DNA (Comparative Example 1) with the use of a nucleic acid delivery reagent (Lipofectamine 3000) (DNA/Lipo3000); the vertical axis indicates the relative value of the intensity of the fluorescence (average value) originating with the FAM that had been attached to the polynucleotide; the bar over each column indicates the standard error;  above a column indicates that the P value relative to "N.A." is less than 0.01; * indicates that the P value relative to "N.A." is less than 0.001; # indicates that the P value relative to "DNA/Lipo3000" is less than 0.05; ## indicates that the P value relative to "DNA/Lipo3000" is less than 0.01; and ### indicates that the P value relative to "DNA/Lipo3000" is less them 0.001.

In the present Description, the terms "contain" and "comprise/include" encompass the concepts of "contain", "comprise/include", "substantially consist of", and "consist of".

1. Modified Polynucleotide and Modifying Molecule

In one embodiment the present invention relates to a modified polynucleotide modified by a molecule that contains the structure represented by general formula (1):

[Chem. 3]

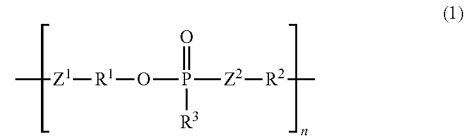

(This modified polynucleotide is also referred to in this Description as the "modified polynucleotide according to the present invention") and to a molecule for modifying a polynucleotide, the molecule containing the structure (This molecule is also referred to in this Description as the "modifying molecule according to the present invention"). A description of this is provided in the following.

$R^1$ and $R^2$ are identical or different and represent a single bond or a divalent group optionally containing at least one group selected from the group consisting of —S—S— and —SH.

The divalent group represented by $R^1$ and $R^2$ can be exemplified by a group capable of functioning as a linker (also referred to herebelow simply as a "linker"), a ring-derived group, and a group in which two or more of these are connected.

The linker can be exemplified by alkylene groups, alkenylene groups, and heteroalkylene groups (for example, heteroalkylene groups that contain —S—S— in the main chain, heteroalkylene groups that contain —NH—COO— in the main chain, and so forth). The linker includes both straight chain configurations and branched chain configurations with straight chain configurations being preferred. The number of atoms constituting the main chain of the linker (the number of carbon atoms in the case of an alkylene group or alkenylene group) is not particularly limited and can be exemplified by 3 to 10, preferably 3 to 6, and more preferably 3 or 4. The linker is preferably an alkylene group, more preferably an alkylene group having 3 to 6 carbon atoms, still more preferably an alkylene group having 3 or 4 carbons, and even more preferably a straight chain alkylene group having 3 or 4 carbons. Specific examples of such alkylene groups are the n-propylene group, isopropylene group, n-butylene group, and isobutylene group.

The ring-derived group is a divalent group in which two hydrogen atoms have been removed from the ring, but is not otherwise particularly limited. There are no particular limitations on the ring, and monocyclic and dicyclic are preferred with monocyclic being more preferred. There are no particular limitations on the atoms constituting the ring and, for example, the ring may be only carbon atoms or may be constituted of the carbon atom and a heteroatom (for example, the nitrogen atom, sulfur atom, oxygen atom, and so forth). The number of atoms constituting the ring is not particularly limited and can be exemplified by 3 to 20, preferably 3 to 12, more preferably 4 to 8, and still more preferably 5 to 7. Such rings can be exemplified by rings having —S—S— in the ring structure, cycloalkanes, cycloalkenes, benzene, naphthalene, and so forth, wherein rings having —S—S— in the ring structure sure preferred. Rings having —S—S— in the ring structure can be specifically exemplified by rings provided by replacing one —C—C— in a cycloalkane or cycloalkene (preferably a cycloalkane) with —S—S—.

$R^1$ is preferably a divalent group optionally containing at least one group selected from the group consisting of —S—S— and —SH, wherein alkylene groups and groups derived from a ring having —S—S— in the ring structure are more preferred and alkylene groups are still more preferred.

$R^2$ is preferably a single bond.

$R^3$ represents —O⁻ or —O—$R^{31}$.

$R^{31}$ represents a monovalent group optionally containing at least one group selected from the group consisting of —S—S— and —SH. The monovalent group represented by $R^{31}$ can be exemplified by alkyl groups, alkenyl groups, heteroalkyl groups (for example, heteroalkyl groups that contain —S—S— in the main chain, heteroalkyl groups that contain —NH—COO— in the main chain, and so forth), the aforementioned ring-derived groups, and groups in which two or more of these are connected. The monovalent group represented by $R^{31}$ encompasses both straight chain configurations and branched chain configurations. The number of atoms constituting the main chain of the monovalent group represented by $R^{31}$ is not particularly limited and can be exemplified by 1 to 20, preferably 3 to 12, and more preferably 5 to 9.

The group represented by —O—$R^{31a}$—S—S—$R^{31b}$ is a preferred example of —O—$R^{31}$.

$R^{31a}$ represents an alkylene group or —$R^{311a}$—NH—COO—$R^{312a}$— ($R^{311a}$ and $R^{312a}$ independently represent an alkylene group). $R^{31a}$ is preferably an alkylene group.

The alkylene group represented by $R^{31a}$ encompasses both straight chain configurations and branched chain configurations wherein straight chain configurations are preferred. The number of carbon atoms in this alkylene group is not particularly limited and, for example, is 3 to 10, preferably 3 to 6, and more preferably 3 or 4. Specific examples of such alkylene groups are the n-propylene group, isopropylene group, n-butylene group, and isobutylene group.

The alkylene groups represented by $R^{311a}$ and $R^{312a}$ encompass both straight chain configurations and branched chain configurations wherein straight chain configurations are preferred. The number of carbon atoms in these alkylene groups is not particularly limited and, for example, is 2 to 10, preferably 2 to 6, and more preferably 2 or 3. Specific examples of such alkylene groups are the ethylene group, n-propylene group, isopropylene group, n-butylene group, and isobutylene group.

$R^{31b}$ represents a protecting group. There are no particular limitations on the protecting group as long as it can function to protect the disulfide bond, and examples are alkyl groups, aryl groups, and so forth.

The alkyl group represented by $R^{31b}$ encompasses both straight chain configurations and branched chain configurations. This alkyl group is preferably a branched chain alkyl group. The number of carbons in this alkyl group is not particularly limited and, for example, is 1 to 6, preferably 2 to 5, more preferably 3 to 5, and even more preferably 4. Specific examples of this alkyl group are the methyl group, ethyl group, n-propyl group, isopropyl group, n-butyl group, isobutyl group, tert-butyl group, sec-butyl group, n-pentyl group, neopentyl group, n-hexyl group, and 3-methylpentyl group. The tert-butyl group is preferred among the preceding.

The aryl group represented by $R^{31b}$ is not particularly limited, but preferably has 6 to 12 carbons, more preferably 6 to 12 carbons, and still more preferably 6 to 8 carbons. This aryl group may be monocyclic or polycyclic (for example, dicyclic, tricyclic, and so forth) wherein monocyclic is preferred. This aryl group can be specifically exemplified by the phenyl group, naphthyl group, biphenyl group, pentalenyl group, indenyl group, anthranyl group, tetracenyl group, pentacenyl group, pyrenyl group, perylenyl group, fluorenyl group, and phenanthryl group. The phenyl group is preferred among the preceding.

$R^3$ is preferably —O—$R^{31}$ and is more preferably —O—$R^{31}$, —S—S—$R^{31b}$.

In a preferred embodiment of the present invention, the combination of $R^1$, $R^2$, and $R^3$ is preferably as follows:

(A) a combination in which $R^1$ is an alkylene group, $R^2$ is a single bond, and $R^3$ is —O—$R^{31a}$—S—S—$R^{31b}$, wherein $R^{31a}$ represents an alkylene group or —$R^{311a}$—NH—COO—$R^{312a}$—, wherein $R^{311a}$ and $R^{312a}$ are identical or different and represent an alkylene group; and $R^{31b}$ represents a protecting group;

and is more preferably as follows:

(A1) a combination in which $R^1$ is an alkylene group having 3 to 6 carbon atoms, $R^2$ is a single bond, and $R^3$ is —O—$R^{31a}$—S—S—$R^{31b}$, wherein $R^{31a}$ represents an alkylene group having 3 to 6 carbon atoms or —$R^{311a}$—NH—COO—$R^{312a}$—, wherein $R^{311a}$ and $R^{312a}$ are identical or different and represent an alkylene group having 2 to 6 carbon atoms; and $R^{31b}$ represents the t-butyl group.

In another preferred embodiment of the present invention, the combination of $R^1$, $R^2$, and $R^3$ is preferably as follows:

(B) a combination in which $R^1$ is a group derived from a ring having a group represented by —S—S— in the ring structure, $R^2$ is a single bond, and $R^3$ is —O⁻;

and is more preferably as follows:

(B1) a combination in which $R^1$ is a group derived from a 4- to 8-membered ring having a group represented by —S—S— in the ring structure, $R^2$ is a single bond, and $R^3$ is —O⁻. Among the preceding combinations of $R^1$, $R^2$, and $R^3$, combinations (A) and (A1) are preferred and combination (A1) is more preferred.

At least one of the aforementioned $R^1$, $R^2$, and $R^3$ contains at least one group selected from the group consisting of —S—S— and —SH. In other words, the structure represented by general formula (1) excludes the case in which all of these $R^1$, $R^2$, and $R^3$ simultaneously do not contain at least one group selected from the group consisting of —S—S— and —SH.

$Z^1$ and $Z^2$ are identical or different and represent —O— or —NH—. Preferably at least one of $Z^1$ and $Z^2$ is —O—, and more preferably both of $Z^1$ and $Z^2$ are —O—.

Any integer is represented by n. For example, n is 1 to 50, preferably 1 to 30, more preferably 3 to 30, still more preferably 5 to 20, even more preferably 7 to 20, and particularly preferably 8 to 15.

The phrase "comprising modification by a molecule that contains the structure represented by general formula (1)" means that the polynucleotide is provided by modification with this molecule.

There are no particular limitations on the mode of modification. The modified polynucleotide according to the present invention is preferably a modified polynucleotide in which the structure represented by general formula (1) is connected to a terminal of the polynucleotide and is more preferably a modified polynucleotide in which the structure represented by general formula (1) is connected to the 5' terminal of the polynucleotide. The structure represented by general formula (1) may also be connected to both terminals of the polynucleotide.

There are no particular limitations on the directionality of the structure presented by general formula (1). For example, the directionality may be such that $Z^1$ is the 5' side of the modified polynucleotide and $R^2$ is the 3' side of the modified polynucleotide. The directionality may also be reversed, i.e., $Z^1$ may be the 3' side of the modified polynucleotide and $R^2$ may be the 5' side of the modified polynucleotide.

Other molecules (for example, fluorescent labels and so forth) may or may not be connected to a terminal $Z^1$ or $R^2$ in the modified polynucleotide according to the present invention. A hydrogen atom is generally bonded in the latter case. In addition, $Z^1$ or $R^2$ may be connected to the polynucleotide that is the modification target (preferably to a terminal nucleotide).

There are no particular limitations on the polynucleotide that is the modification target, and, in addition to DNA, RNA, and so forth, known chemical modifications may be carried out as in the following examples. In order to prevent degradation by hydrolases, e.g., nucleases, the phosphate residue (phosphate) at the individual nucleotides can be replaced by a chemically modified phosphate residue, for example, phosphorothioate (PS), methylphosphonate, phosphorodithionate, and so forth. The hydroxyl group at position 2 on the sugar (ribose) of each ribonucleotide may be changed to —OR (R represents, for example, $CH_3$ (2'-O-Me), $CH_2CH_2OCH_3$ (2'-O-MOE), $CH_2CH_2NHC(NH)NH_2$, $CH_2CONHCH_3$, $CH_2CH_2CN$, and so forth). In addition, a chemical modification of the base moiety (pyrimidine, purine) may also be carried out; for example, a methyl group or a cationic functional group may be introduced at position 5 on a pyrimidine base, or the carbonyl group at position 2 may be changed to a thiocarbonyl group. Moreover, the phosphate moiety and/or a hydroxyl moiety can be modified with, for example, biotin, an amino group, a lower alkylamine group, an acetyl group, and so forth, but there is no limitation to these. A BNA (LNA), in which the conformation of the sugar moiety is locked in the N form by bridging the 2' oxygen and the 4' carbon of the sugar moiety of the nucleotide, can preferably also be used.

The polynucleotide that is the modification target may have another molecule connected to it. This other molecule can be exemplified by fluorescent labels.

The base length of the polynucleotide that is the modification target is not particularly limited and can be exemplified by a base length of not more than 500, preferably a base length of not more than 200, more preferably a base length of not more than 100, still more preferably a base length of not more than 50, and even more preferably a base length of not more than 30. The lower limit is not particularly limited, and examples thereof are a base length of 5, a base length of 10, and a base length of 15.

The polynucleotide that is the modification target is preferably one for which the main objective is use through delivery into a cell. Polynucleotides with such an objective can be exemplified by polynucleotides such as antisense polynucleotides, siRNA, miRNA, miRNA precursors, aptamers, guide RNA, mRNA, and so forth.

The modified polynucleotide according to the present invention and the modifying molecule according to the present invention can be synthesized in accordance with or based on a known method. For example, production can be carried out by carrying out nucleic acid synthesis by the phosphoramidite method using a phosphoramidite monomer that can form the structure given by general formula (1). For the case in which $R^1$ is a divalent group optionally containing at least one group selected from the group consisting of —S—S— and —SH and $R^2$ is a single bond, a specific example is a method in which nucleic acid synthesis is carried out by the phosphoramidite method according to or based on the usual procedures, using, for example, a compound represented by general formula (2):

[Chem. 4]

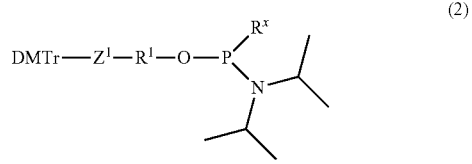

[In the formula, DMTr represents the dimethoxytrityl group. $R^x$ represents —O—$R^{31}$ or —O—$(CH_2)_2$—CN. The other symbols are the same as described in the preceding.] as the phosphoramidite monomer.

After the completion of synthesis, the product can be isolated and purified by the usual methods, e.g., chromatographic methods and so forth. The structure of the product can be identified using, for example, elemental analysis, MS (FD-MS) analysis, IR analysis, $^1$H-NMR, $^{13}$C-NMR, and so forth.

2. Applications

The modified polynucleotide according to the present invention, because it by itself efficiently passes through the cell membrane, can be efficiently introduced into a cell even without the formation of a complex with, e.g., a cationic lipid. The modified polynucleotide according to the present invention also has a relatively low cytotoxicity. As a consequence, the modified polynucleotide according to the present invention can be used in a variety of applications where an objective is the delivery of the modified polynucleotide into a cell, for example, for a delivery agent for delivery into a cell, or for a drug or reagent and so forth (these are also collectively referred to in the following as the "agent according to the present invention").

The agent according to the present invention contains the modified polynucleotide according to the present invention but is not otherwise particularly limited, and it may contain other components on an optional basis. This other component should be a pharmaceutically acceptable component but is not otherwise particularly limited, and examples here are base substances, carriers, solvents, dispersants, emulsifying agents, buffers, stabilizers, excipients, binders, disintegrants, lubricants, thickeners, humectants, colorants, fragrances, chelating agents, and so forth.

There are no particular limitations on the mode of use of the agent according to the present invention, and the appropriate mode of use can be adopted in conformity with the particular type of agent according to the present invention. The agent according to the present invention can be vised, for example, in vitro (for example, addition to a cell culture medium) or in vivo (for example, administration to an animal).

The target for application of the agent according to the present invention is not particularly limited and can be exemplified by various mammals, e.g., human, monkey, mouse, rat, dog, cat, rabbit, and so forth; and by animal cells.

The cell type is also not particularly limited and can be exemplified by blood cells, hematopoietic stem cells/progenitor cells, gametes (spermatozoa, oocytes), fibroblasts, epithelial cells, vascular endothelial cells, nerve cells, hepatocytes, keratinocytes, muscle cells, epidermal cells, endocrine cells, ES cells, iPS cells, tissue stem cells, cancer cells, and so forth.

When the agent according to the present invention is used as an anticancer agent, the type of cancer cell in this case is not particularly limited and can be exemplified by kidney cancer cells, leukemia cells, esophageal cancer cells, stomach cancer cells, colon cancer cells, liver cancer cells, pancreatic cancer cells, lung cancer cells, prostate cancer cells, skin cancer cells, breast cancer cells, cervical cancer cells, and so forth.

The dosage form of the agent according to the present invention is not particularly limited and the appropriate dosage form can be adopted in conformity to the mode of use. For example, in the case of administration to an animal, examples are oral agents such as tablets, capsules, granules, powders, fine granules, syrups, enteric tablets, slow-release capsules, chewable tablets, drops, pills, liquids for internal use, lozenges, sustained-release tablets, sustained-release granules, and so forth; and external preparations, e.g., nasal drops, inhalants, rectal suppositories, inserts, enemas, jellies, and so forth. The agent according to the present invention may be a solid agent, semisolid agent, or liquid agent.

The content of the modified polynucleotide according to the present invention in the agent according to the present invention will depend on, for example, the mode of use, the target for application, conditions for the intended application, and so forth, and is thus not limited; however, it can be, for example, 0.0001 to 95 wt % and can preferably be 0.001 to 50 wt %.

The dosage in the case of administration of the agent according to the present invention to an animal should be an effective amount that expresses drug efficacy, but is not otherwise particularly limited. Under ordinary circumstances, in the case of oral administration the weight of the modified polynucleotide according to the present invention as the effective ingredient is generally 0.1 to 1,000 mg/kg-body weight per day and is preferably 0.5 to 50 mg/kg-body weight per day, while in the case of parenteral administration it is 0.01 to 100 mg/kg-body weight per day and is preferably 0.1 to 10 mg/kg-body weight per day. This dosage preferably is administered once a day or is divided into two or three administrations per day, and may also be increased or decreased as appropriate depending on age, disease state, and symptoms.

EXAMPLES

The present invention is described in detail in the following based on examples; however, the present invention is not limited by these examples.

Reference Example 1. Synthesis of DTT-Type Phosphoramidite Monomer

DTT-type phosphoramidite monomer (compound 5) was synthesized using the following synthesis scheme.

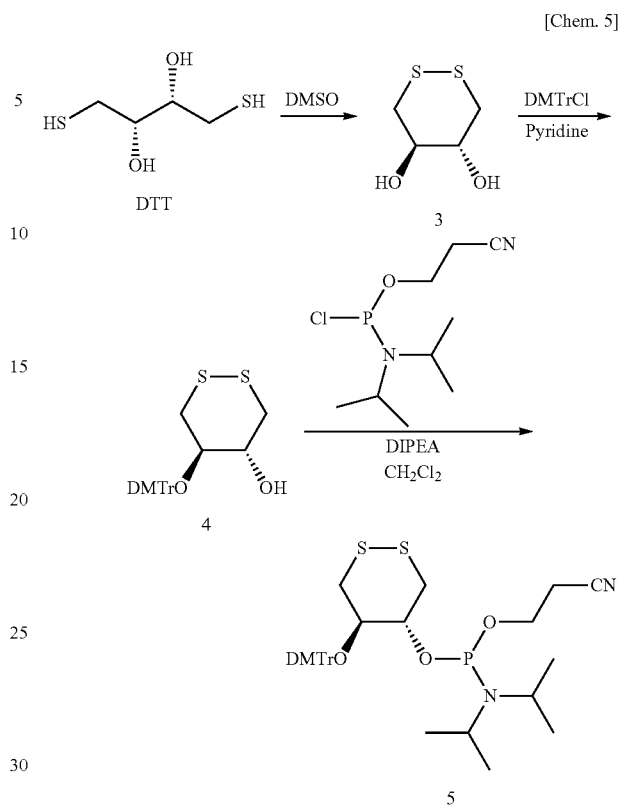

[Chem. 5]

Synthesis of Compound 3

Dimethyl sulfoxide (0.78 mL) was added to dithiothreitol (DTT) (1.54 g, 10.0 mmol) and stirring was carried out for 4 hours at 110° C.

After cooling to room temperature, the produced solid was suspended in dichloromethane and was filtered off by suction filtration. The filtered-off solid was washed with a small amount of ethyl acetate and was dried in a vacuum to obtain the target compound 3 as a white solid (1.26 g, 82%).

$^1$H-NMR (400 MHz, DMSO-d$_6$) δ: 5.24 (2H, d, J=3.2 Hz), 3.33 (2H, br. s), 3.03 (2H, d, J=13.2 Hz), 2.74 (1H, d, J=13.2 Hz), 2.72 (1H, d, J=13.6 Hz).

Synthesis of Compound 4

Compound 3 (1 g, 6.57 mmol) was azeotroped twice with methanol and then twice with anhydrous pyridine. The residue was dissolved in anhydrous pyridine (15 mL), dimethoxytrityl chloride (3.0 g, 8.85 mmol) was added, and stirring was carried out at room temperature. After 4 hours, another addition of dimethoxytrityl chloride (2.0 g, 5.90 mmol) was made and stirring was carried out at room temperature. After 4 hours, methanol was added to the reaction solution and concentration was then carried out under reduced pressure. The residue was dissolved in ethyl acetate and washing was carried out with water and then a saturated aqueous sodium chloride solution. The organic layer was dried over anhydrous sodium sulfate and concentration under reduced pressure was performed. The resulting residue was purified by neutral flash silica gel column chromatography (hexane/ethyl acetate=90:10+1% triethylamine→80:20+1% triethylamine) to obtain the target compound 4 as a white foamy solid (1.67 g, 56%).

ESI-MS: calcd. for $C_{25}H_{26}NaO_4S_2$ 477.1170 $[M+Na]^+$; found: 477.1262 $[M+Na]^+$.

Synthesis of Compound 5

Compound 4 (300 mg, 0.66 mmol) was azeotroped twice with anhydrous acetonitrile. The residue was dissolved in dichloromethane (2 mL), N,N-diisopropylethylamine (350 μL, 1.98 mmol) was added, and 2-cyanoethyl N,N-diisopropylchlorophosphoramidite (217 μL, 0.99 mmol) was added dropwise at 0° C. with stirring. After 20 minutes, the reaction solution was diluted with ethyl acetate and washing with water and then a saturated aqueous sodium chloride solution was performed. The organic layer was dried over anhydrous sodium sulfate and was concentrated under reduced pressure. The resulting residue was purified by neutral flash silica gel column chromatography (hexane/ethyl acetate=20:1, +1% triethylamine→8:1, +1% triethylamine) to obtain the target compound 5 as a white foamy solid (280 mg, 65%).

$^{31}$P-NMR (121 MHz, $CDCl_3$) δ: 148.4, 148.1

ESI-MS: calcd. for $C_{34}H_{43}N_2NaO_5PS_2$ 677.2249 $[M+Na]^+$; found: 677.2134 $[M+Na]^+$.

Reference Example 2. Synthesis of ThioL-Type Phosphoramidite Monomer

A ThioL-type phosphoramidite monomer (compound 4) was synthesized according to the following synthesis scheme. 3-mercaptopropanol was used as the starting material, and compound 1 was obtained by conversion of the thiol group to the disulfide structure. The ThioL-type phosphoramidite monomer 4 was obtained by coupling with the separately synthesized C3 linker derivative 3.

[Chem. 6]

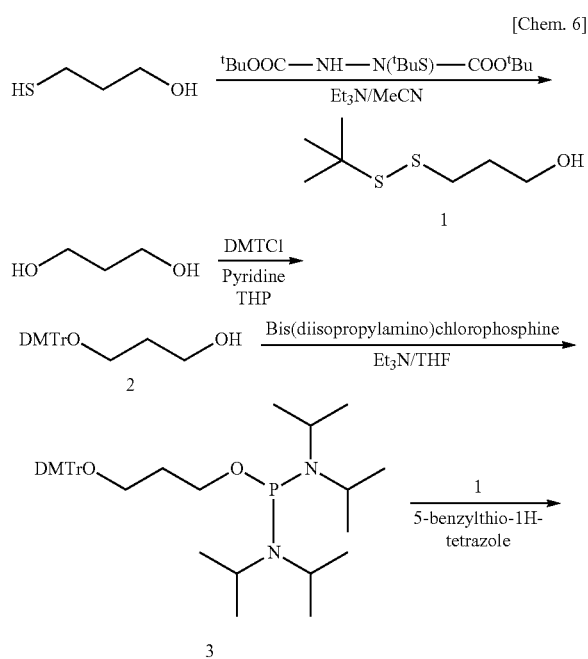

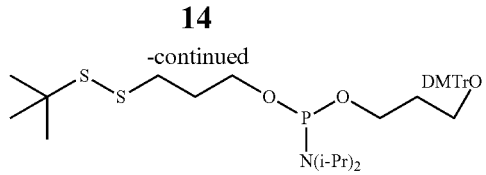

4

Synthesis of Compound 1

3-Mercaptopropanol (808 μL, 9.36 mmol) was added dropwise while stirring under an argon atmosphere to an acetonitrile solution (36 mL) of di-tert-butyl 1-(tert-butylthio)-1,2-hydrazinedicarboxylate (3.0 g, 9.36 mmol) and triethylamine (1.09 mL, 7.80 mmol). After stirring overnight at room temperature, the reaction solution was concentrated under reduced pressure. Hexane (10 mL) was added to the resulting residue and the produced precipitate was filtered off and removed and the filtrate was concentrated under reduced pressure. The residue was purified by neutral flash silica gel column chromatography (toluene/ethyl acetate=15:1) to obtain the target compound 1 as a light yellow oily material (731 mg, 85%).

$^1$H-NMR (400 MHz, $CDCl_3$) δ: 3.75 (2H, t, J=6.0 Hz), 2.82 (2H, t, J=7.2 Hz), 1.93 (2H, m, J=6.8 Hz), 1.33 (s, 9H).

Synthesis of Compound 2

A pyridine solution (20 mL) of dimethoxytrityl chloride (3.0 g, 9.10 mmol) was added to a pyridine solution (52 mL) of propanediol (13 mL, 181.0 mmol) and stirring was performed at room temperature. After 26 hours, the reaction solution was concentrated under reduced pressure and then dissolved in ethyl acetate (20 mL) and washing was carried out twice with water (80 mL) and then with a saturated aqueous sodium chloride solution. The organic layer was dried over anhydrous sodium sulfate and then concentrated under reduced pressure. The resulting residue was purified by neutral flash silica gel column chromatography (hexane/ethyl acetate=3:1→1:1) to obtain the target compound 2 as a white solid (2.50 g, 83%).

$^3$H-NMR (400 MHz, $CDCl_3$) δ: 7.43-7.38 (2H, m), 7.33-7.26 (5H, m), 7.24-7.16 (2H, m), 6.79-6.85 (4H, m), 3.87 (1H, t, J=5.6 Hz), 3.79 (3H, s), 3.78 (3H, s), 3.28 (1H, t, J=5.6 Hz), 1.91-1.80 (2H, m), 1.60 (1H, br. s)

ESI-MS: calcd. for $C_{24}H_{26}NaO_4$ 401.1723 $[M+Na]^+$; found: 401.176 $[M+Na]^+$.

Synthesis of Compound 4

An anhydrous tetrahydrofuran solution (3 mL) of compound 2 (300 mg, 0.79 mmol) was added dropwise at 0° C. to an anhydrous tetrahydrofuran solution (5 mL) of bis(N,N-diisopropylamino)chlorophosphine (240 mg, 0.79 mmol) and triethylamine (120 μL). The reaction solution was stirred at room temperature and after 100 minutes the completion of the reaction was confirmed by $^{31}$P-NMR (from 135.5 ppm to 121.8 ppm, $C_6D_6$). Compound 1 (142 mg, 0.79 mmol) and then an acetonitrile solution (0.25 M, 750 μL) of 5-benzylthio-1H-tetrazole were added to the reaction solution. The reaction solution was stirred at room temperature, and after 80 minutes the completion of the reaction was confirmed by $^{31}$P-NMR (from 121.8 ppm to 147.0 ppm, $C_6D_6$). The reaction solution was diluted with ethyl acetate (70 mL) followed by washing twice with a saturated aqueous sodium bicarbonate solution (70 mL), water (70 mL), and then a saturated aqueous sodium chloride solution (70 mL). The organic layer was concentrated under reduced pressure and the resulting residue was purified by neutral flash silica gel column chromatography (hexane/ethyl acetate=15:1, +1% triethylamine) to obtain the target compound 4 as a light yellow oily material (189 mg, 63%).

$^{31}$P-NMR (121 MHz, C$_6$D$_6$) δ: 146.97
$^3$H-NMR (400 MHz, C$_6$D$_6$) δ: 7.68 (d, 2H, J=11.0 Hz), 7.51 (4H, d, J=11.2 Hz), 7.19 (3H, d, J=11.4 Hz), 6.79 (4H, d, J=11 Hz), 3.31 (14H, m), 2.11 (2H, m), 1.92 (2H, m), 1.19 (9H, s, 3CH$_3$; 12H, d, 3CH$_3$)
$^{13}$C-NMR (100 MHz, C$_6$D$_6$) δ: 158.7, 145.9, 136.7, 130.2, 128.4, 127.7, 126.5, 113.1, 86.0, 61.6, 61.4, 60.4, 54.4, 47.1, 42.8, 37.2, 32.2, 31.1, 29.6, 24.5
ESI-MS: calcd. for C$_{37}$H$_{54}$NO$_5$PS$_2$, 598.276 [M-C$_4$H$_9$S]$^+$ found: 598.277 [M-C$_4$H$_9$S]$^+$.

Example 1. Synthesis of DTT-Type Modified Polynucleotide (5DTT-DNA

A DTT-type modified polynucleotide (5DTT-DNA) in which the 5'-terminal of DMA composed of the base sequence given by 5'-AACCGCTTCCCOGACTTCC (SEQ ID NO:1) was ligated with the structure given by the following formula (A):

[Chem.7]

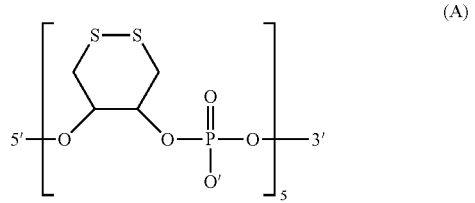

(A)

and the 3'-terminal was fluorescent labelled (FAM label), was synthesized by a conventional method using a DNA/RNA solid-phase synthesizer (NTS M-2-MX, Nihon Techno Service Co., Ltd.) and using β-cyanoethyl phosphoramidite (Glen Research), the DTT-type phosphoramidite monomer (Reference Example 1), and 6-FAM. SEQ ID NO:1 is an antisense sequence of the luciferase gene originating from *P. pyralis*. The obtained modified polynucleotide was subjected to cleavage from the resin and deprotection by conventional methods and was purified by high-performance liquid chromatography. Column: C18Hydrosphere 10×250 mm (YMC Co., Ltd.); column temperature: room temperature; measurement wavelength: 260 nm; mobile phase: 50 mM triethylammonium acetate buffer (pH 7.0) (+5% acetonitrile)/acetonitrile=100:0→70:30 (20 min, linear gradient).

The modified polynucleotide-containing fraction was isolated and then concentrated using a centrifugal evaporator. Structural determination was performed using mass analysis (MALDI-TOF MS). The obtained modified polynucleotide was dissolved in ultrapure water and suitably diluted and the UV absorption spectrum was then measured and the concentration was determined.

MALDI-MS: calcd. 7361.628 [M+H]$^+$; found: 7362.888 [M+H]$^+$.

Example 2. Synthesis of DTT-Type Modified Polynucleotide (10DTT-DNA

A DTT-type modified polynucleotide (10DTT-DNA) in which the 5'-terminal of DNA composed of the base sequence given by SEQ ID NO:1 was ligated with the structure given by the following formula (B):

[Chem. 8]

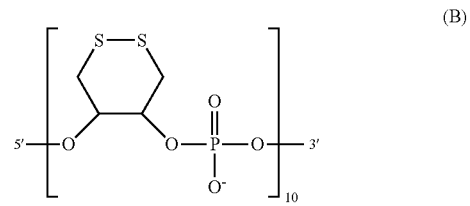

(B)

and the 3'-terminal was fluorescent labelled (FAM label), was synthesized proceeding as in Example 1.

MALDI-MS: calcd. 8434.762 [M+H]$^+$; found: 8434.22 [M+H]$^+$.

Example 3. Synthesis of ThioL-Type Modified Polynucleotide (5ThioL-DNA

A ThioL-type modified polynucleotide (5ThioL-DNA) in which the 5'-terminal of DNA composed of the base sequence given by SEQ ID NO:1 was ligated with the structure given by the following formula (C):

[Chem. 9]

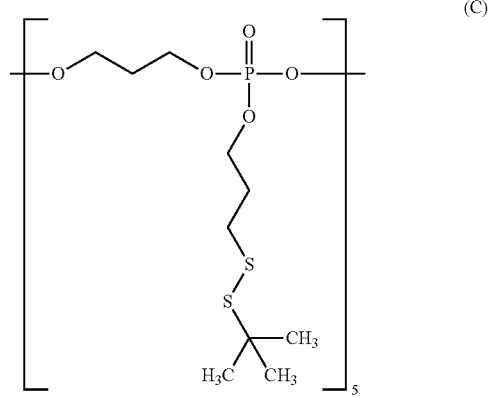

(C)

and the 3'-terminal was fluorescent labelled (FAM label), was synthesized proceeding as in Example 1, but using the ThioL-type phosphoramidite monomer (Reference Example 2) in place of the DTT-type phosphoramidite monomer (Reference Example 1).

MALDI-MS: calcd. 7789.695 [M+H]$^+$; found: 7789.289 [M+H]$^+$.

Example 4. Synthesis of ThioL-Type Modified Polynucleotide (10ThioL-DNA

A ThioL-type modified polynucleotide (10ThioL-DNA) in which the 5'-terminal of DNA composed of the base sequence given by SEQ ID NO:1 was ligated with the structure given by the following formula (D):

[Chem. 10]

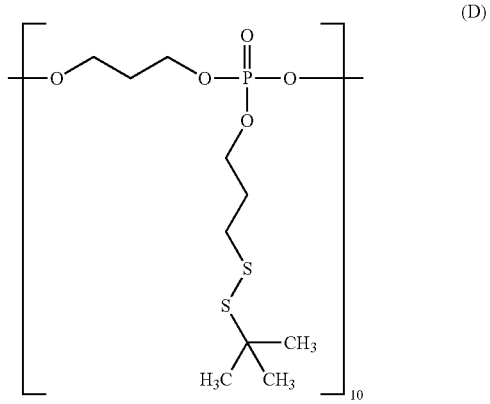

and the 3'-terminal was fluorescent labelled (FAM label), was synthesized proceeding as in Example 3.

MALDI-MS: calcd. 9287.426 [M+H]$^+$; found: 9288.527 [M+H]$^+$.

Cooperative Example 1. Synthesis of Unmodified Polynucleotide (DMA

DNA (DNA) composed of the base sequence given by SEQ ID NO:1 and having a fluorescent-labelled 3'-terminal (FAM label) was synthesized by a conventional method.

MALDI-MS: calcd. 6212.113 [M+H]$^+$; found: 6212.705 [M+H]$^+$.

Comparative Example 2. Synthesis of Unmodified Polynucleotide (R-DNA

DNA (R-DNA) composed of the base sequence given by 5'-ACACGTCCTCTCAGCCCTC (SEQ ID NO:2) and having a fluorescent-labelled 3'-terminal (FAM label) was synthesized by a conventional method.

Comparative Example 3. Synthesis of Phosphorothioate DNA (PS-DNA

Phosphorothioate DNA (PS-DNA) composed of the base sequence given by SEQ ID NO:1 and having a fluorescent-labelled 3'-terminal (FAM label) was synthesized by a conventional method.

MALDI-MS: calcd. 6499.02 [M+H]$^+$; found: 6502.773 [M+H]$^+$.

Teat Example 1. Call Membrane Permeability Teat 1

The FAM-labelled polynucleotides according to the examples and comparative examples were respectively added to culture media and the cell membrane permeability of the polynucleotides was checked by measurement of the cellular fluorescence intensity (=amount of polynucleotide uptake into the cells). This was specifically carried out as follows.

pGL3 (Promega Corporation) and pTK-Green Renilla Luc (Thermo Fisher Scientific Inc.), which are expression plasmids for luciferase derived from Photinus pyralis and Renilla reniformis, were introduced into HeLa cells. This was cultured in the presence of G418 and puromycin to establish HeLa-LucRluc, a cell line that stably expresses luciferase. This HeLa cell was cultured on DMEM culture medium (Wako Pure Chemical Industries, Ltd.) supplemented with 10% fetal bovine serum (FBS), 100 U/mL penicillin, and 100 jig/mL streptomycin. The culture conditions were 37° C. at a humidity of 95% under air with a 5% $CO_2$ concentration. $2 \times 10^4$ HeLa p13 cells were seeded to each well of a 12-well plate and culture was carried out for one day. Each of the polynucleotides according to the examples and comparative examples was added to 0.3 mL serum-free DMEM culture medium to provide a concentration of 1 µM and mixing was performed. The obtained liquid mixture was added to the culture medium and incubation was carried out for 3 hours. For the positive control, on the other hand, a nucleic acid delivery reagent (Lipofectamine 3000, Invitrogen) was used and the unmodified polynucleotide of Comparative Example 1 was added to the culture medium in accordance with the directions of the reagent instructions and incubation was carried out. After the completion of incubation, the cells were rinsed with culture medium and detachment was carried out using a trypsin treatment. The FAM-based fluorescence intensity of the obtained cells was measured by flow cytometry (BD FACSCanto II, Becton, Dickinson and Company). A greater fluorescence intensity here indicates that more (FAM-labelled) polynucleotide permeates across the cell membrane and is delivered into the cell.

The results are given in FIG. 1. The DNA (Comparative Example 1) exhibited almost no membrane permeability. It was shown, on the other hand, that the DTT (Examples 1 and 2) and ThioL (Examples 3 and 4) were each uptaken into the cells. In particular, it was shown that 10ThioL (Example 4) was uptaken into the cells at at least 2-fold relative to the use of the commercial Lipofectamine 3000.

Test Example 2. Antisense Sequence-Induced Expression Inhibition Test 1

Polynucleotides according to the examples and comparative examples, which had an antisense sequence for the luciferase gene originating from P. pyralis, were added to the culture medium and the amount of luciferase expression was measured. This served to check whether the polynucleotide permeated across the cell membrane and was able to express its function (gene expression-inhibiting effect as an antisense nucleic acid). This was specifically carried out as follows.

The HeLa-LucRluc cells (HeLa cells that stably express P. pyralis luciferase and Renilla luciferase) were cultured on DMEM culture medium (Wako Pure Chemical Industries, Ltd.) supplemented with 10% fetal bovine serum (FBS), 100 U/mL penicillin, and 100 jig/mL streptomycin. The culture conditions were 37° C. at a humidity of 95% under air with a 5% $CO_2$ concentration. $2 \times 10^4$ HeLa-LucRluc cells were seeded to each well of a 12-well plate and culture was carried out for one day. Each of the polynucleotides of the examples and comparative examples was added to 0.3 mL serum-free DMEM culture medium to provide a concentration of 1 µM and mixing was performed. The obtained liquid mixture was added to the culture medium and incubation was carried out. On the other hand, a nucleic acid delivery reagent (Lipofectamine 3000, Invitrogen) was used and each of the polynucleotides of Example 4 and Comparative Examples 1 and 3 was added to the culture medium in accordance with the directions of the Reagent Instructions and incubation was carried out. After the completion of incubation, the cells were dissolved with Reporter Lysis Buffer (Promega Corporation). The luciferase activity (P.

*pyralis* luciferase activity and *Renilla* luciferase activity) of the resulting cell lysate solution was measured using a luminometer (Luminescencer-PSN, ATTO Corporation) and Luciferase Assay Reagent (Promega Corporation).

Figure 2:
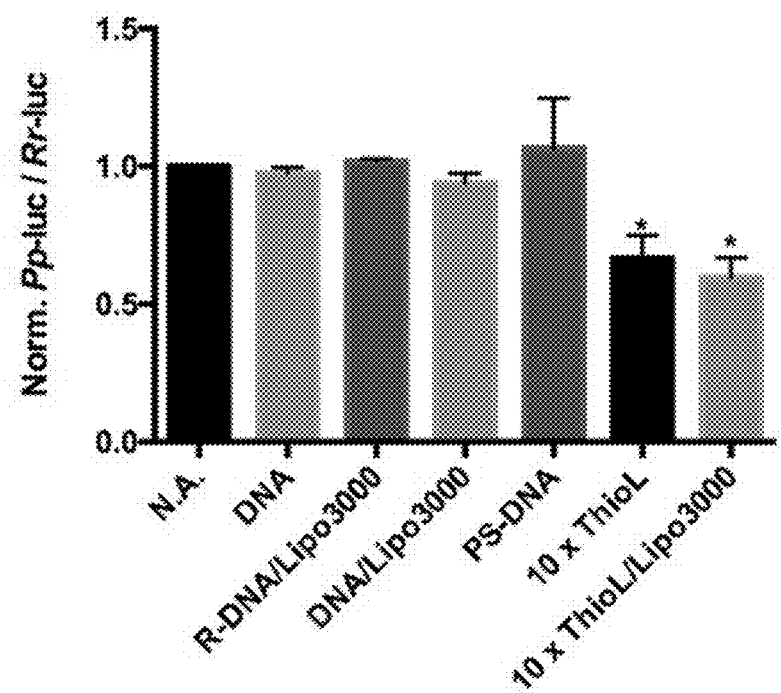
FIG. 2 shows the results of the expression inhibition test of Test Example 2, where the horizontal axis gives the case of no addition of polynucleotide to the culture medium as "N.A.", the cases of the addition to the culture medium of the polynucleotide of Examples or Comparative Examples as such (DNA (Comparative Example 1), PS-DNA (Comparative Example 3), 10ThioL (Example 4)), and the cases of the addition to the culture medium of the DNA (Comparative Example 1), R-DNA (Comparative Example 2), or 10ThioL (Example 4) with the use of a nucleic acid delivery reagent (Lipofectamine 3000) (-/Lipo3000); the vertical axis indicates the relative value of the luciferase activity ratio (*P. pyralis* luciferase activity value/*Renilla* luciferase activity value) (average value); the bar over each column indicates the standard error; for the individual columns, * indicates that the P value relative to "N.A." is less than 0.05.

The results are given in FIG. 2. The appearance of a gene expression-inhibiting effect was entirely absent for DNA/Lipo3000 and PS-DNA (Comparative Example 3), while 10ThioL (Example 4) provided a gene expression-inhibiting effect. This shows that the present procedure can be more effective than liposomes as a procedure for introducing polynucleotides into cells.

Test Example 3. Cytotoxicity Test 1

The cytotoxicity of the polynucleotides of the examples and comparative examples was checked using an MTT assay. This was specifically carried out as follows.

HeLa-LucRluc cells (HeLa cells that stably express *P. pyralis* luciferase and *Renilla* luciferase) were cultured on DMEM culture medium (Wako Pure Chemical Industries, Ltd.) supplemented with 10% fetal bovine serum (FBS), 100 U/mL penicillin, and 100 µg/mL streptomycin. The culture conditions were 37° C. at a humidity of 95% under air with a 5% 00a concentration. $2 \times 10^4$ HeLa-LucRluc cells were seeded to each well of a 96-well plate and culture was carried out for one day. Each of the polynucleotides according to the examples and comparative examples was added to 0.3 mL serum-free DMEM culture medium to provide a concentration of 1 µM or 5 µM and mixing was performed. The obtained liquid mixture was added to the culture medium and incubation was carried out. For the positive control, on the other hand, a nucleic acid delivery reagent (Lipofectamine 3000, Invitrogen) was used and the unmodified polynucleotide of Comparative Example 1 was added to the culture medium in accordance with the directions of the Reagent Instructions and incubation was carried out. After incubation for 24 hours, 20 µL of CellTiter 96 (registered trademark) AQueous One Solution Reagent (Promega Corporation) was added and incubation was carried out for 2.5 hours. The absorbance at 490 nm was measured using a 96-well plate reader. A higher absorbance indicates a lower cytotoxicity for the added polynucleotide.

Figure 3:
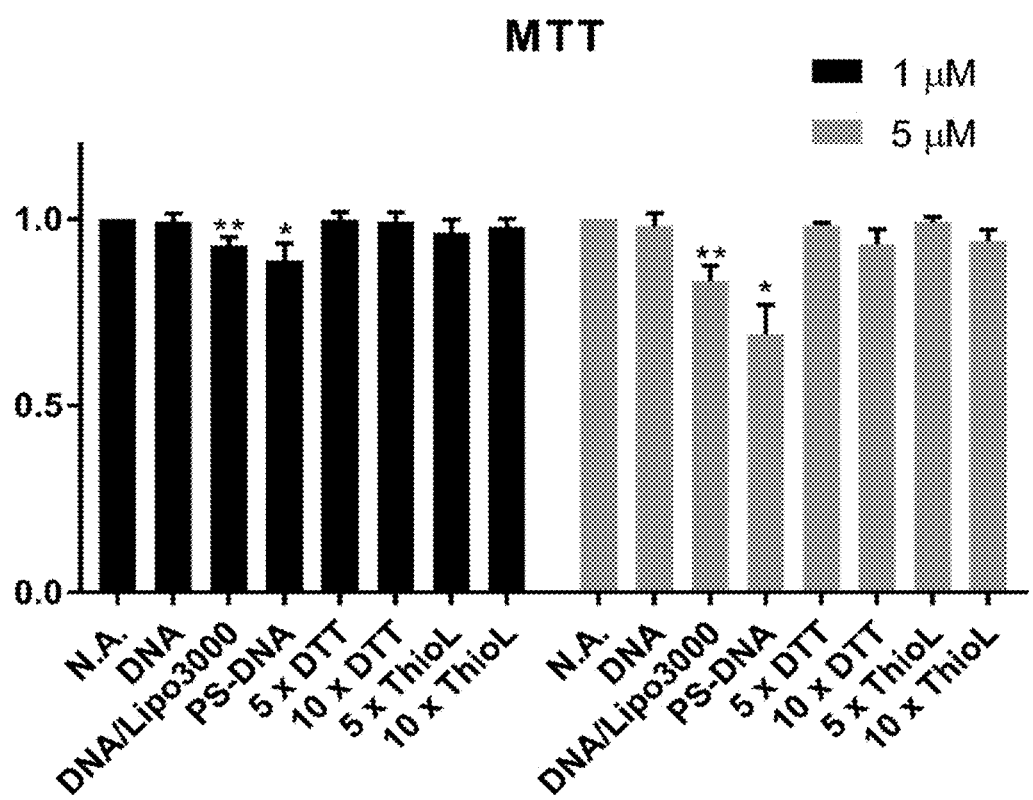
FIG. 3 gives the results of the cytotoxicity test of Test Example 3, where the horizontal axis gives the case of no addition of polynucleotide to the culture medium as "N.A.", the cases of the addition to the culture medium of the polynucleotide of Examples or Comparative Examples as such (DNA (Comparative Example 1), PS-DNA (Comparative Example 3), 5×DTT (Example 1), 10×DTT (Example 2), 5× ThioL (Example 3), 10× ThioL (Example 4)), and the case of the addition to the culture medium of the DNA (Comparative Example 1) with the use of a nucleic acid delivery reagent (Lipofectamine 3000) (DNA/Lipo3000); the vertical axis indicates the relative value of the absorbance (average value); the black columns refer to a polynucleotide concentration in the polynucleotide solution of 1 µM, and the grey columns refer to 5 for this concentration; the bar over each column indicates the standard error; * above a column indicates that the P value relative to "N.A." is less than 0.05;  indicates that the P value relative to "N.A." is less than 0.01; and * indicates that the P value relative to "N.A." is less than 0.001.

The results are given in FIG. 3. DNA/Lipo3000 and PS-DNA (Comparative Example 3) exhibited toxicity, but toxicity was not exhibited by the polynucleotides of the examples (5×DTT (Example 1), 10×DTT (Example 2), 5× ThioL (Example 3), 10× ThioL (Example 4)). The conclusion can therefore be drawn that the polynucleotides of the examples have a low toxicity.

Example 5. Synthesis of ThioL-Type Modified Polynucleotide (5× tBu-PS-DNA

A ThioL-type modified polynucleotide (5× tBu-PS-DNA) in which the 5'-terminal of a PS-DNA composed of 5'-CGGTATCCAGATCCACAAC (SEQ ID NO:3) was ligated with the structure given by the following formula (C):

[Chem. 11]

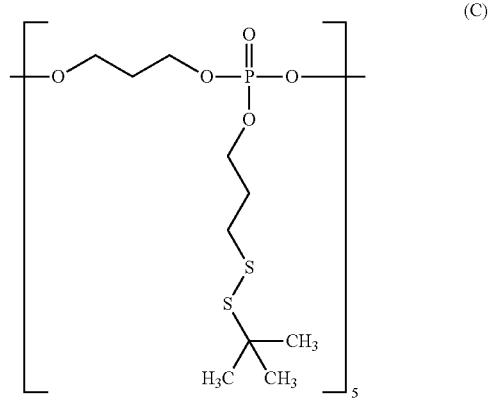

and the 3'-terminal was fluorescent labelled (FAM label), was synthesized proceeding as in Example 3.

Example 6. Synthesis of ThioL-Type Modified Polynucleotide (10× tBu-PS-DNA

A ThioL-type modified polynucleotide (10× tBu-PS-DNA) in which the 5'-terminal of PS-DNA composed of the base sequence given by SEQ ID NO:3 was ligated with the structure given by the following formula (D):

[Chem.12]

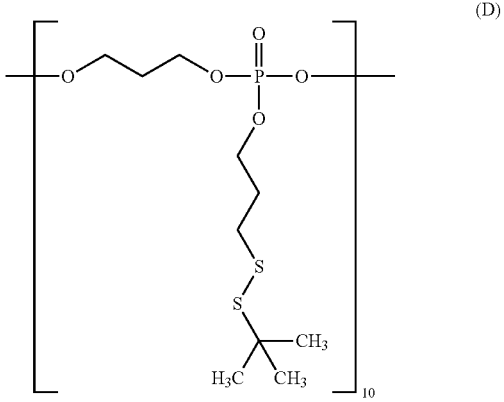

and the 3'-terminal was fluorescent labelled (FAM label), was synthesized proceeding as in Example 3.

Comparative Example 4. Synthesis of Phosphorothioate DNA (PS-ENA

Phosphorothioate DNA (PS-DNA) composed of the base sequence given by SEQ ID NO:3 and having a fluorescent-labelled 3'-terminal (FAM label) was synthesized by a conventional method.

Example 7. Synthesis of ThioL-Type siRNA (5× ThioL siRNA (3' & 3'

A ThioL-type modified single-strand RNA (5× ThioL guide strand (3')) in which the 3'-terminal of RNA composed of 5'-UUUOGAAGUACUCAGCGUAAGUU (SEQ ID NO:4) was ligated with the structure given by the following formula (C):

[Chem.13]

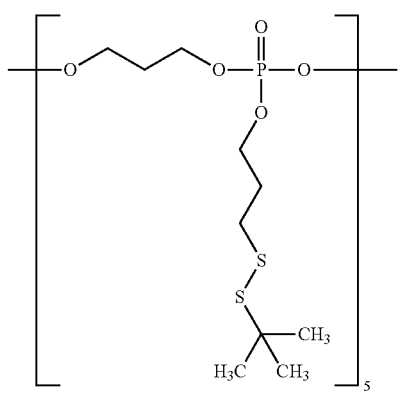

was synthesized proceeding as in Example 3.

On the other hand, a ThioL-type modified single-strand RNA (5× ThioL passenger strand (3')) in which the 3'-terminal of RNA composed of 5'-CUUACGCUGAGUAC-UUCGAAAUU (SEQ ID NO:5) was ligated with the structure given by the following formula (C):

[Chem. 14]

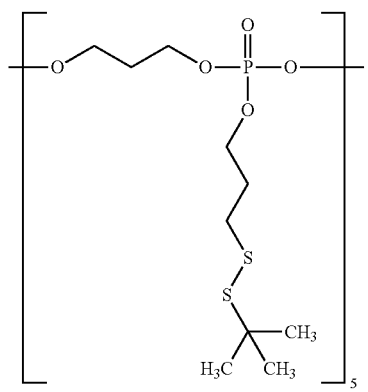

was synthesized proceeding as in Example 3.

The 5× ThioL guide strand (3') and the 5× ThioL passenger strand (3') were mixed followed by holding for 3 minutes at 90° C. in 1× annealing buffer (60 mM KCl, 6 mM HEPES-KOH pH 7.5, 0.2 mM MgCl$_2$) with adjustment to provide the target concentration (0.1 to 1 µM); this was followed by standing at quiescence for 3 hours until return to room temperature to form double-strand RNA (ThioL-type siRNA (5× ThioL siRNA (3' & 3'))).

Example 8. Synthesis of ThioL-Type siRNA (5× ThioL siRNA (3' & 5'

A ThioL-type modified single-strand RNA (5× ThioL passenger strand (5')) in which the 5'-terminal of RNA composed of the base sequence given by SEQ ID NO:5 was ligated with the structure given by the following formula (C):

[Chem. 15]

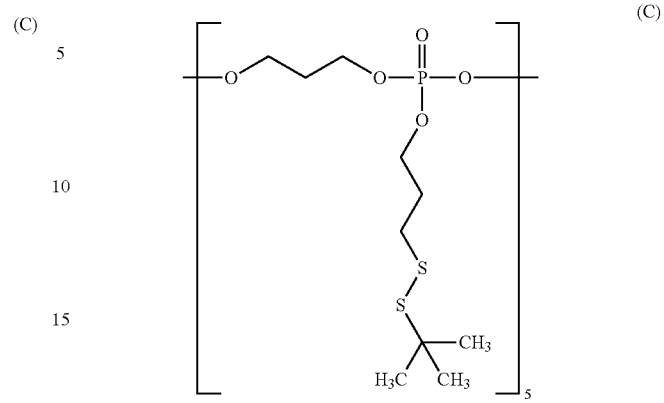

was synthesized proceeding as in Example 3.

The 5× ThioL guide strand (3') and the 5× ThioL passenger strand (5') were mixed followed by holding for 3 minutes at 90° C. in 1× annealing buffer (60 mM KCl, 6 mM HEPES-KOH pH 7.5, 0.2 mM MgCl$_2$) with adjustment to provide the target concentration (0.1 to 1 µM); this was followed by standing at quiescence for 3 hours until return to room temperature to form double-strand RNA (ThioL-type siRNA (5× ThioL siRNA (3' & 5'))).

Comparative Example 5. Synthesis of Unmodified siRNA

RNA composed of the base sequence given by SEQ ID NO:4 and RNA composed of the base sequence given by SEQ ID NO:5 were synthesized by a conventional method and a double strand (unmodified siRNA) was formed proceeding as in Example 7.

Test Example 4. Cell Membrane Permeability Test 2

This was carried out as in Test Example 1, but vising the antisense polynucleotides of Example 5, Example 6, and Comparative Example 4 as the polynucleotide. 100 nM was used for the polynucleotide concentration.

Figure 4:
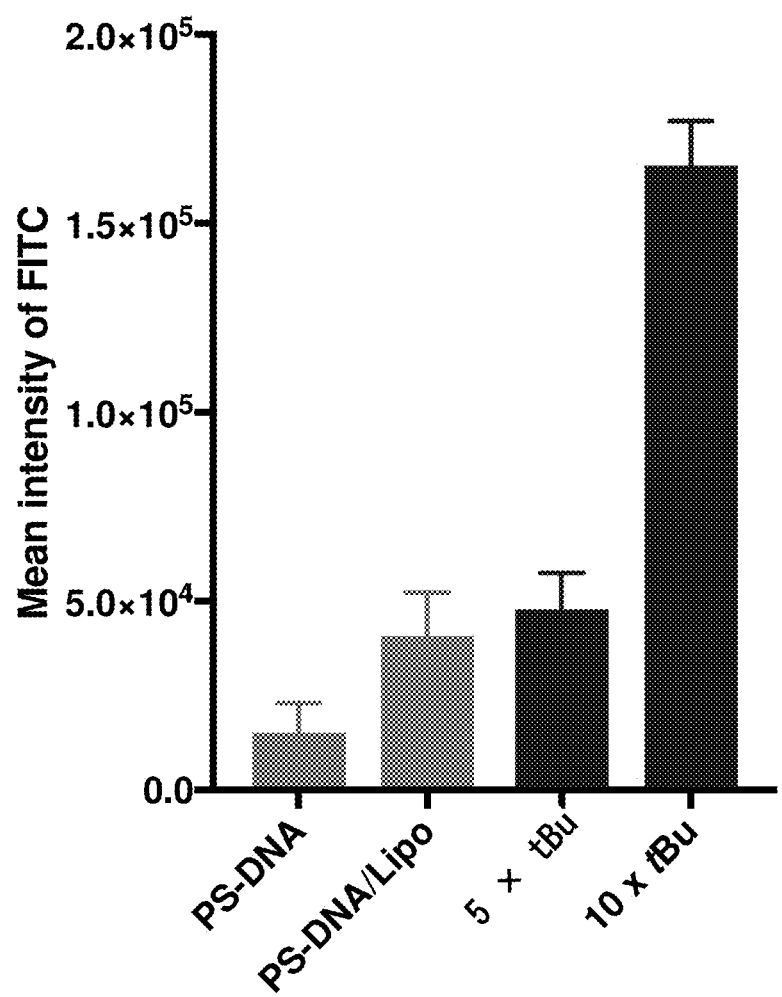
FIG. 4 gives the results of the cell membrane permeability test of Test Example 4, where the horizontal axis gives the cases of the addition to the culture medium of the polynucleotide of the Examples or Comparative Example as such (PS-DNA (Comparative Example 4), 5× tBu (Example 5), 10× tBu (Example 6)), and the case of the addition to the culture medium of PS-DNA (Comparative Example 4) with the use of a nucleic acid delivery reagent (Lipofectamine 3000) (PS-DNA/Lipo); the vertical axis indicates the intensity of the fluorescence (average value) originating with the FAM that had been attached to the polynucleotide; and the bar over each column indicates the standard error.

The results are given in FIG. 4. The ThioL modifications exhibited a cell membrane permeability that was equal to or better than that exhibited for the use of the commercial Lipofectamine 3000.

Test Example 5. Antisense Sequence-Induced Expression Inhibition Test 2

This was carried out proceeding as in Test Example 2, but using the antisense polynucleotides of Example 5 and Comparative Example 4 as the polynucleotide. 1 µM was used for the polynucleotide concentration.

Figure 5:
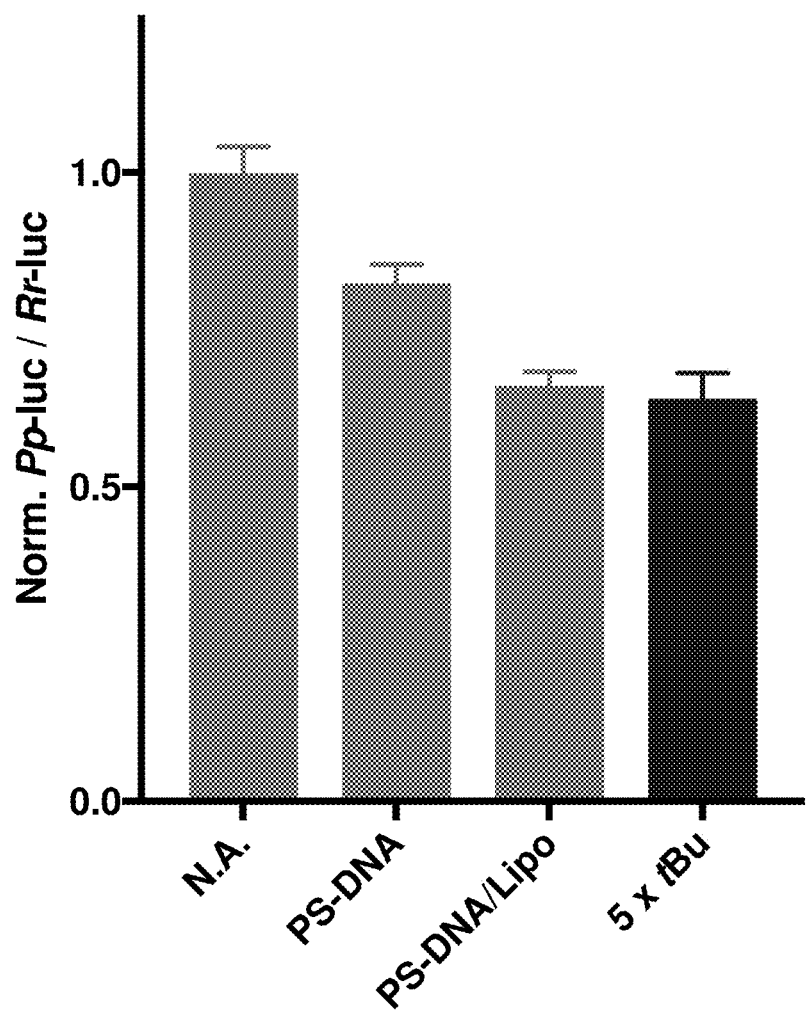
FIG. 5 shows the results of the expression inhibition test of Test Example 5, where the horizontal axis gives the case of no addition of polynucleotide to the culture medium as "N. A.", the cases of the addition to the culture medium of the polynucleotide of Example or Comparative Example as such (PS-DNA (Comparative Example 4), 5× tBu (Example 5)), and the case of the addition to the culture medium of PS-DNA (Comparative Example 4) with the use of a nucleic acid delivery reagent (Lipofectamine 3000) (PS-DNA/Lipo); the vertical axis indicates the relative value of the luciferase activity ratio (*P. pyralis* luciferase activity value/*Renilla* luciferase activity value) (average value); and the bar over each column indicates the standard error.

The results are given in FIG. 5. The ThioL modification exhibited the same gene expression-inhibiting effect as for the use of the commercial Lipofectamine 3000.

Test Example 6. Cytotoxicity Test 2

This was carried out proceeding as in Test Example 3, but using the antisense polynucleotides of Example 5 and Comparative Example 4 as the polynucleotide. 5 µM was used for the polynucleotide concentration.

Figure 6:
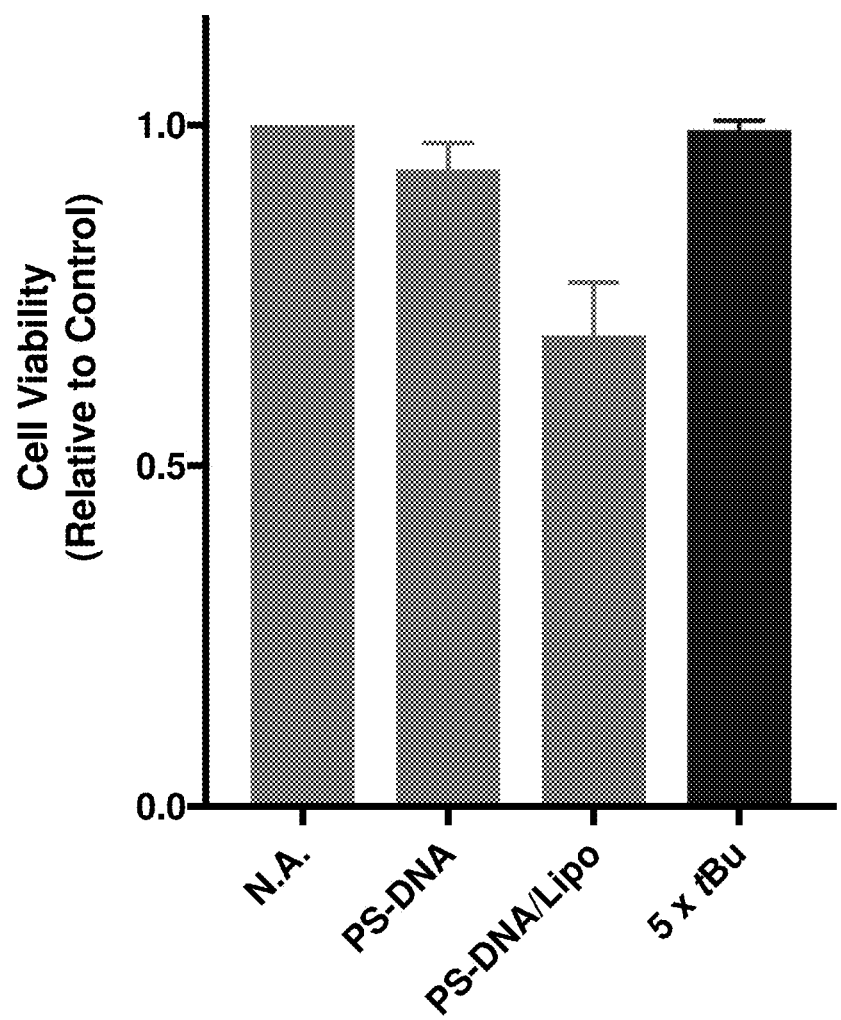
FIG. 6 gives the results of the cytotoxicity test of Test Example 6, where the horizontal axis gives the case of no addition of polynucleotide to the culture medium as "N.A.", the cases of the addition to the culture medium of the polynucleotide of Example or Comparative Example as such (PS-DNA (Comparative Example 4), 5× tBu (Example 5)), and the case of the addition to the culture medium of PS-DNA (Comparative Example 4) with the use of a nucleic acid delivery reagent (Lipofectamine 3000) (PS-DNA/Lipo); the vertical axis indicates the relative value of the absorbance (average value); and the bar over each column indicates the standard error.

The results are given in FIG. 6. The polynucleotide according to the example (5× tBu-PS-DNA) did not exhibit cytotoxicity.

Test Example 7. siRNA-mediated Expression Inhibition Test 1

This was carried out proceeding as in Test Example 2, but using the siRNAs of Example 7, Example 8, and Comparative Example 5 as the polynucleotide. 1 μM or 100 nM was used for the polynucleotide concentration.

Figure 7:
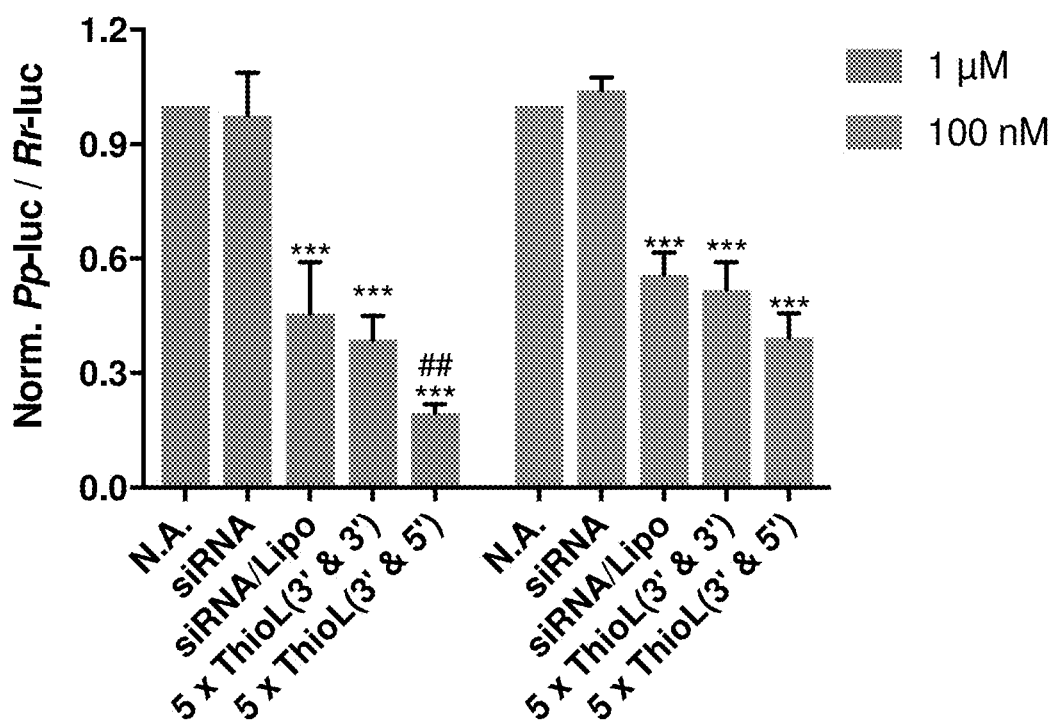
FIG. 7 shows the results of the expression inhibition test of Test Example 7, where the horizontal axis gives the case of no addition of polynucleotide to the culture medium as "N.A.", the cases of the addition to the culture medium of the polynucleotide of Examples or Comparative Example as such (siRNA (Comparative Example 5), 5× ThioL (3' & 3') (Example 7), 5× ThioL (3' & 5') (Example 8)), and the case of the addition to the culture medium of siRNA (Comparative Example 5) with the use of a nucleic acid delivery reagent (Lipofectamine 3000) (siRNA/Lipo); the vertical axis indicates the relative value of the luciferase activity ratio (*P. pyralis* luciferase activity value/*Renilla* luciferase activity value) (average value); the bar over each column indicates the standard error; *** indicates that the P value relative to "N.A." is less than 0.001; and ## indicates that the P value relative to "siRNA/Lipo" is less than 0.01.

The results are given in FIG. 7. The ThioL modifications exhibited a gene expression-inhibiting effect that was equal to or better than that for the use of the commercial Lipofectamine 3000.

Reference Example 3. Synthesis of Procationic Phosphoramidite Monomer

A procationic phosphoramidite monomer (compound 4) was synthesized according to the synthesis scheme given below.

[Chem.16]

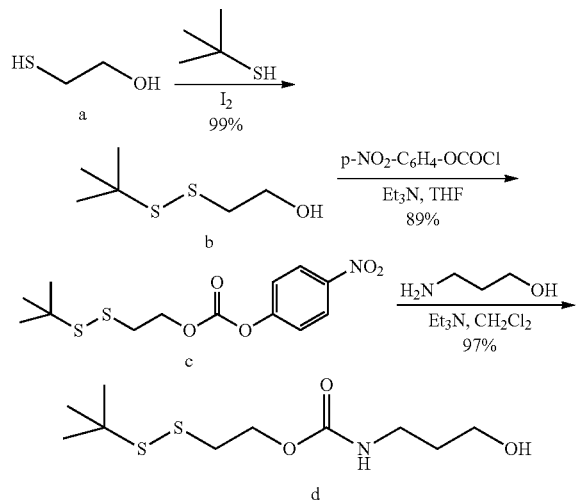

[Chem.17]

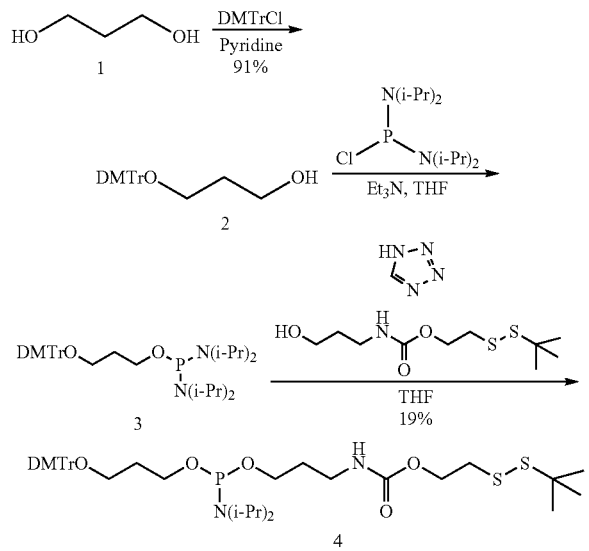

Synthesis of Compound B:
2-(tert-butyldisulfanyl)ethanol 2-methyl-2-propanethiol (12 mL, 230 mmol, 10 eq.) was added to 100% ethanol (22 mL) and 2-mercaptoethanol (0.77 mL, 23 mmol, 1.0 eq.) and this was stirred on an ice bath. $I_2$ (3.0 g, 36.8 mmol, 1.1 eq.) was dissolved in 100% ethanol (17 mL) and this was added dropwise until the color of the reaction solution changed from colorless to red, followed by reaction overnight. $NaHCO_3$ (saturated, 23 mL) was added until the pH reached 7 or above and distillation under reduced pressure was carried out. AcOEt was added, liquid/liquid separation was carried out against 10% $Na_2S_2O_5$ and brine, and the organic layer was distilled off under reduced pressure. Purification was performed by column chromatography (neutral flash, hexane/AcOEt=2/1) to obtain compound b as an oil (1.62 g, 9.72 mmol, 91%). $^1$H-NMR (400 MHz, $CDCl_3$): δ 3.842 (2H, t, J=6.0 Hz), 2.827 (2H, t, J=6.0 Hz), 1.317 (9H, s). Various other spectral data were in good agreement with data described in the literature (Tetrahedron, 2005, 61, 6138).

Synthesis of Compound C:
2-(tert-butyldisulfanyl)ethyl 4-nitrophenyl carbonate 4-nitrophenyl chloroformate (9.89 g, 49.1 mmol, 1.5 eq.) and THF (10 mL) were added to compound b (5.45 g, 32.8 mmol, 1.0 eq.) and a reaction was run on an ice bath under an argon atmosphere. TEA (6.8 mL) and dried THF (25 mL) were added dropwise; a reaction was run for 10 minutes on an ice bath; and a reaction was then run for 18 hours at room temperature. The reaction solution was filtered and washed (hexane/AcOEt=5/1) and distillation was performed under reduced pressure. Column chromatography (neutral flash, hexane/AcOEt=4/1) was performed to obtain compound c (9.69 g, 29.2 mmol, 89%). $^1$H-NMR (400 MHz, $CDCl_3$): δ 8.27 (2H, m), 7.37 (2H, m), 4.51 (3H, t, J=6.8 Hz), 2.99 (3H, t, J=6.8 Hz), 1.34 (9H, s). Various other spectral data were in good agreement with data described in the literature (Angew. Chem. Int. Ed., 2012, 51, 10347).

Synthesis of Compound D:
2-(tert-butyldisulfanyel)ethyl
(3-hydroxypropyl)carbamate $CH_2Cl_2$ (15 mL) containing TEA (6.4 mL) and compound c (9.15 g, 27.6 mmol, 1.0 eq.) was added to $CH_2Cl_2$ (25 mL) containing 3-amino-1-propanol (3.2 mL, 41.4 mmol, 1.0 eq.) and stirring was performed at room temperature for 1 hour. The following were then carried out: distillation under reduced pressure; dissolution in AcOEt (15 mL); washing with water, saturated $NaHCO_3$, 0.1 M NaOH, and brine; drying over $Na_2SO_4$, and distillation under reduced pressure. Compound 4 was obtained as an oil (7.49 g, 27.0 mmol, 97%). $^1$H-NMR (400 MHz, $CDCl_3$): δ 4.28 (2H, t, J=6.4 Hz), 3.67 (2H, t, J=5.6 Hz), 3.13 (2H, t, J=6.0 Hz), 2.88 (2H, t, J=6.4 Hz), 1.69 (2H, t, J=6.0 Hz), 1.31 (9H, s); $^{13}$C-NMR (100 MHz, $CDCl_3$): δ 157.22, 63.24, 59.60, 48.04, 39.19, 37.77, 32.55, 29.92; HRMS (ESI) calcd. for $C_{10}H_{21}NO_3S_2$ [M+Na]$^+$: 290.10; found for 290.0913.

Synthesis of Compound 2: 3-(4,4'-dimethoxytrityl)propan-1-ol 4,4'-dimethoxytrityl chloride (3.09 mg, 9.12 mmol) was dissolved in pyridine (72 mL), and propan-1,3-diol (13 mL, 181 mmol) was added under an argon atmosphere and stirring was carried out for 5.5 hours. The solvent was distilled off under reduced pressure and the residue was extracted with $Et_2O/H_2O$. The organic layer was dried over $Na_2SO_4$ and the solvent was distilled off under reduced pressure. The residue was purified by column chromatography (hexane/AcOEt=3/1→1/1, 1% TEA) to obtain compound 2 as a yellow oily material (1.58 g, 3.28 mmol, 65%). $^3$H-NMR (400 MHz, CDCl$_3$): δ 7.43-7.40 (2H, m), 7.33-7.20 (7H, m), 6.88-6.78 (4H, m), 3.82-3.74 (8H, m), 3.27 (2H, q, J=5.6 Hz), 2.24 (1H, t, J=5.6 Hz), 1.85 (2H, q, J=5.6). Various other spectral data were in good agreement with data described in the literature.

Synthesis of Compound 4: 2-(tert-butyldisulfaneyl) ethyl (3-(((3-(bis(4-methoxyphenyl)(phenyl)ethoxy) propoxy) (diisopropylamino)phosphaneyl)propyl) carbamate THF (dried, 8 mL) and TEA (dried, 0.5 mL, 3.96 mmol, 1.4 eq.) were added to N,N-bis(diisopropylamino)chlorophosphine (776 mg, 2.91 mmol, 1.0 eq.) that had been azeotroped with pyridine. THF (dried, 3 mL) was added to compound 2 (1.06 mg, 2.8 mmol, 1.0 eq.); this was added dropwise at 0° C. under an argon atmosphere; and a reaction was then run for 2 hours at room temperature. THF (dried, 4 mL) was added to compound 4 (530 mg, 1.99 mmol, 0.7 eq.) that had been azeotroped with pyridine, and this was added dropwise to the reaction solution at 0° C. under an argon atmosphere. THF (dried, 3 mL) was added to 1H-tetrazole (95.5 mg, 1.36 mmol, 0.5 eq.) and this was also added dropwise and a reaction was run for 2 hours at room temperature.

Liquid/liquid separation was carried out against $CH_2Cl_2$ and $NaHCO_3$, which had been preliminarily cooled to 0° C. The organic layer was distilled off under reduced pressure to obtain a crude yellow oil (2.13 g). Purification by column chromatography (neutral flash, hexane/AcOEt=15/1→10/1, 1% TEA) yielded compound 4 as a colorless oil (284 mg, 0.37 mmol, 19%). $^1$H-NMR (400 MHz, CDCl$_3$): δ 7.24 (9H, m), 6.80 (4H, d), 4.23 (2H, t, J=7.2 Hz), 3.78 (6H, s), 3.59 (6H, m), 3.23 (2H, t, J=6.0 Hz), 3.14 (2H, t, J=6.4 Hz), 2.85 (t, 2H, J=6.8 Hz), 1.91 (t, 2H, J=6.8 Hz), 1.73 (t, 2H, J=6.4 Hz), 1.31 (s, 9H), 1.12 (d, 12H, J=7.2 Hz); $^{13}$C-NMR (100 MHz, CDCl$_3$): δ 158.39, 145.36, 136.62, 130.12, 128.27, 127.73, 126.67, 113.04, 85.85, 62.96, 60.49, 60.36, 47.93, 42.95, 42.82, 39.28, 38.84, 32.04, 31.96, 29.94, 24.72; $^{31}$P-NMR (162 MHz, CDCl$_3$): δ 146.21; HRMS (ESI) calcd. for $C_{40}H_{59}N_2O_7PS_2$ [M+H]$^+$: 775.35; found for 776.3627.

Example 9. Synthesis of Procationic Modified Polynucleotide (5× Cation-PS-DNA

Using the procationic phosphoramidite monomer (Reference Example 3), a procationic modified polynucleotide (5× cation-PS-DNA) in which the 5'-terminal of PS-DMA composed of the base sequence given by SEQ ID NO:1 was ligated with the structure given by the following formula (E):

[Chem. 18]

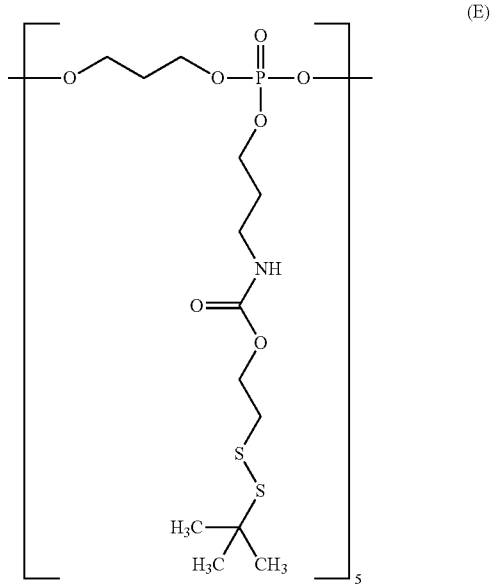

and the 3'-terminal was fluorescent labelled (FAM label), was synthesized proceeding as in Example 1.

Comparative Example 6. Synthesis of Phosphorothioate DNA (PS-DNA

Phosphorothioate DNA (PS-DNA) composed of the base sequence given by SEQ ID NO:1 and having a fluorescent-labelled 3'-terminal (FAM label) was synthesized by a conventional method.

Example 10. Synthesis of Procationic siRNA (5× ThioL siRNA (3' & 3'

Using the procationic phosphoramidite monomer (Reference Example 3), a procationic modified single-strand RNA (5× cation guide strand (3')) in which the 3'-terminal of RNA composed of the base sequence given by SEQ ID NO:4 was ligated with the structure given by the following formula (E):

[Chem. 19]

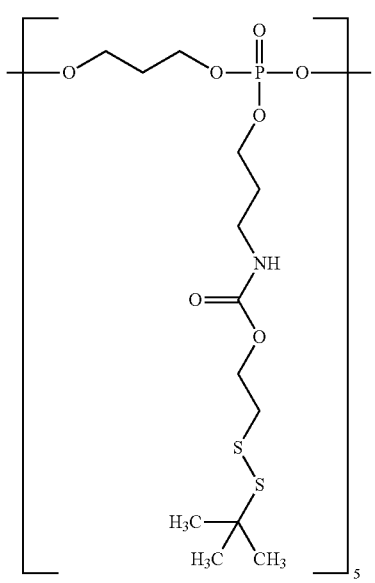

was synthesized proceeding as in Example 1.

On the other hand, using the procationic phosphoramidite monomer (Reference Example 3), a procationic modified single-strand RNA (5× cation passenger strand (3')) in which the 3'-terminal of RNA composed of the base sequence given by SEQ ID NO:5 was ligated with the structure given by the following formula (E):

[Chem. 20]

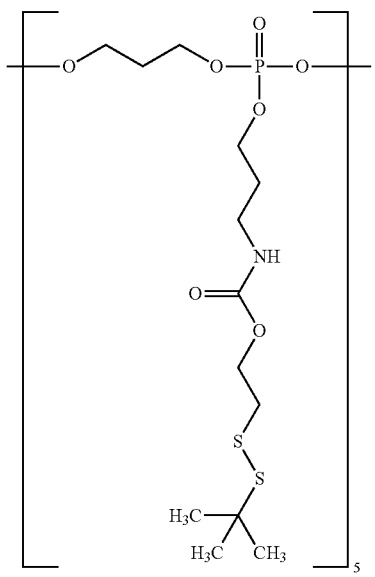

was synthesized proceeding as in Example 1.

The 5× cation guide strand (3') and the 5× cation passenger strand (3') were mixed followed by holding for 3 minutes at 90° C. in 1× annealing buffer (60 mM KCl, 6 mM HEPES-KOH pH 7.5, 0.2 mM MgCl$_2$) with adjustment to provide the target concentration (0.1 to 1 μM); this was followed by standing at quiescence for 3 hours until return to room temperature to form double-strand RNA (procationic siRNA (5× cation siRNA (3' & 3'))).

Example 11. Synthesis of Procationic siRNA (5× Cation siRNA (3' & 5'

Using the procationic phosphoramidite monomer (Reference Example 3), a procationic modified single-strand RNA (5× cation passenger strand (5')) in which the 5'-terminal of RNA composed of the base sequence given by SEQ ID NO:5 was ligated with the structure given by the following formula (E):

[Chem. 21]

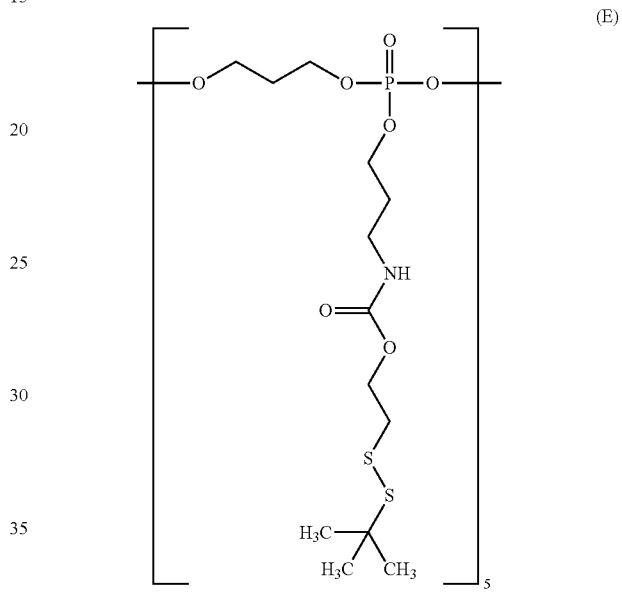

was synthesized proceeding as in Example 1.

The 5× cation guide strand (3') and the 5× cation passenger strand (5') were mixed followed by holding for 3 minutes at 90° C. in 1× annealing buffer (60 mM KCl, 6 mM HEPES-KOH pH 7.5, 0.2 mM MgCl$_2$) with adjustment to provide the target concentration (0.1 to 1 μM); this was followed by standing at quiescence for 3 hours until return to room temperature to form double-strand RNA (procationic siRNA (5× cation siRNA (3' & 5'))).

Test Example 8. Call Membrane Permeability Test 3

This was carried out as in Test Example 1, but using the antisense polynucleotides of Example 9 and Comparative Example 6 as the polynucleotide. 100 nM was used for the polynucleotide concentration.

Figure 8:
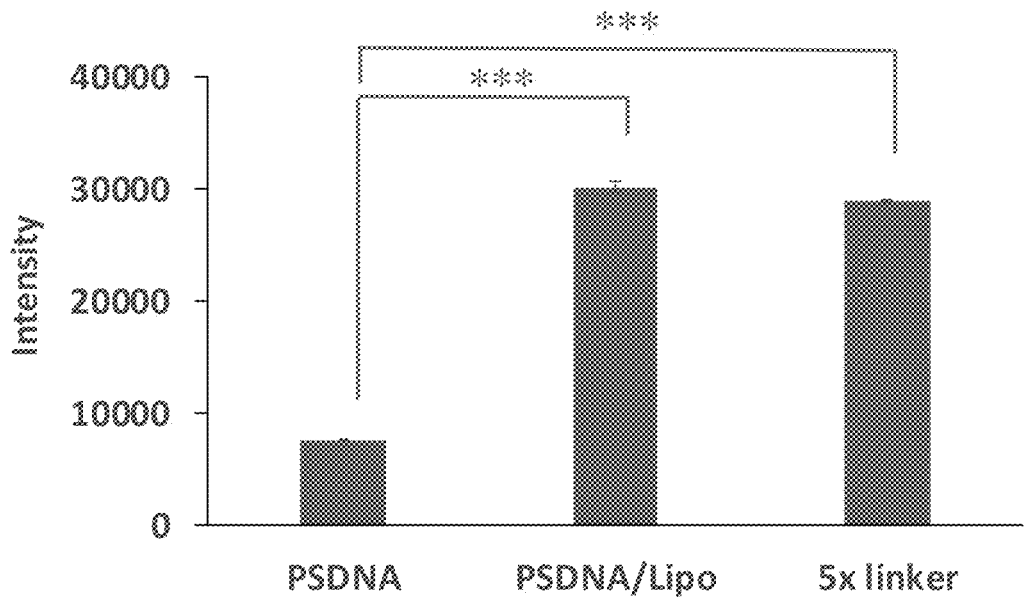
FIG. 8 gives the results of the cell membrane permeability test of Test Example 8, where the horizontal axis gives the cases of the addition to the culture medium of the polynucleotide of Example or Comparative Example as such (PSDNA (Comparative Example 6), 5× linker (Example 9)), and the case of the addition to the culture medium of PSDNA (Comparative Example 6) with the use of a nucleic acid delivery reagent (Lipofectamine 3000) (PSDNA/Lipo); the vertical axis indicates the intensity of the fluorescence (average value) originating with the FAM that had been attached to the polynucleotide; the bar over each column indicates the standard error; and *** indicates that the P value is less than 0.001.

The results are given in FIG. 8. The procation modification exhibited the same cell membrane permeability as for the use of the commercial Lipofectamine 3000.

Test Example 9. Cytotoxicity Test 3

This was carried out as in Test Example 3, but using the antisense polynucleotides of Example 9 and Comparative Example 6 as the polynucleotide. 1 μM was used for the polynucleotide concentration.

Figure 9:
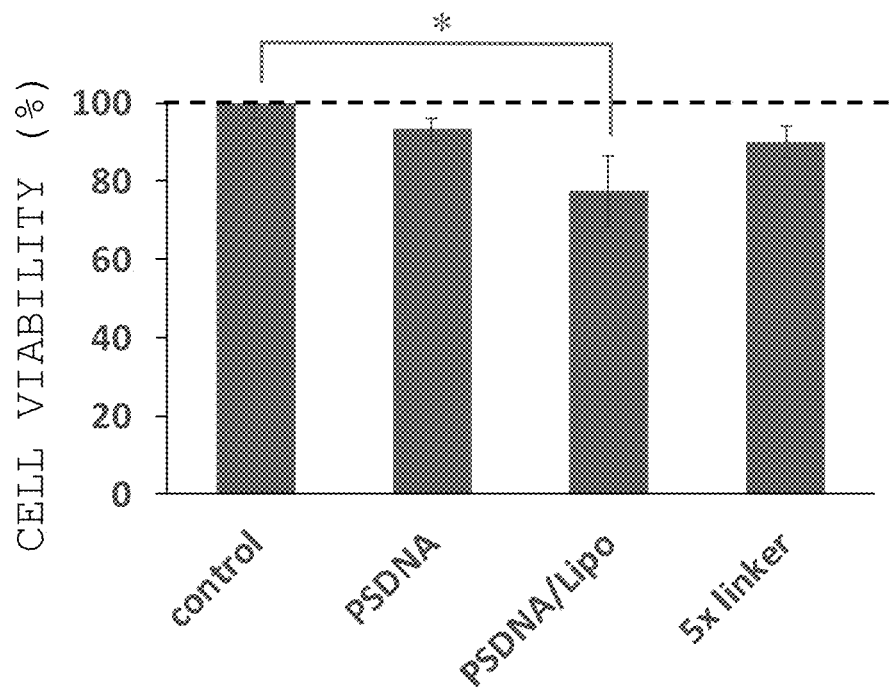
FIG. 9 gives the results of the cytotoxicity test of Test Example 9, where the horizontal axis gives the case of no addition of polynucleotide to the culture medium as "control", the cases of the addition to the culture medium of the polynucleotide of Example or Comparative Example as such (PSDNA (Comparative Example 6), 5× linker (Example 9)), and the case of the addition to the culture medium of PSDNA (Comparative Example 6) with the use of a nucleic acid delivery reagent (Lipofectamine 3000) (PSDNA/Lipo); the vertical axis indicates the relative value of the absorbance (average value); the bar over each column indicates the standard error; and * indicates that the P value is less than 0.05.

The results are given in FIG. 9. The polynucleotide according to the example (5× cation-PS-DNA) did not exhibit cytotoxicity.

The invention claimed is:

1. A method comprising introducing a composition comprising a modified polynucleotide into a cell in vitro or in vivo, wherein the modified polynucleotide is modified by a molecule that contains a structure represented by general formula (1):

[Chem. 1]

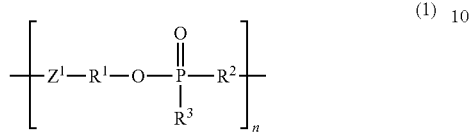 (1)

wherein, $R^1$ and $R^2$ are identical or different and represent a single bond or a divalent group optionally containing at least one group selected from the group consisting of —S—S— and —SH; $R^3$ represents —O— or —O—$R^{31}$, wherein $R^{31}$ represents a monovalent group optionally containing at least one group selected from the group consisting of —S—S— and —SH; $Z^1$ is —O— or —NH—; provided that at least one of $R^1$, $R^2$, and $R^3$ contains at least one group selected from the group consisting of —S—S— and —SH; and n is an integer from 3 to 30, wherein the structure represented by general formula (1) is linked to a terminal of the polynucleotide.

2. The method according to claim 1, wherein $R^1$ is an alkylene group or a group derived from a ring having —S—S— in a structure of the ring, $R^2$ is a single bond, and $R^3$ is —O— or —O—$R^{31a}$—S—S—$R^{31b}$, wherein $R^{31a}$ represents an alkylene group or —$R^{311a}$—NH—COO—$R^{312a}$—, wherein $R^{311a}$ and $R^{312a}$ are identical or different and represent an alkylene group; and $R^{31b}$ represents a protecting group.

3. The method according to claim 1, wherein (A) $R^1$ is an alkylene group, $R^2$ is a single bond, and $R^3$ is —O⁻$R^{31a}$—S—S—$R^{31b}$, wherein $R^{31a}$ represents an alkylene group or —$R^{311a}$—NH—COO—$R^{312a}$—, wherein $R^{311a}$ and $R^{312a}$ are identical or different and represent an alkylene group; and $R^{31b}$ represents a protecting group, or (B) $R^1$ is a group derived from a ring having a group represented by —S—S— in a structure of the ring, $R^2$ is a single bond, and $R^3$ is —O⁻.

4. The method according to claim 1, wherein (A1) $R^1$ is an alkylene group having 3 to 6 carbon atoms, $R^2$ is a single bond, and $R^3$ is —O—$R^{31a}$—S—S—$R^{31b}$, wherein $R^{31a}$ represents an alkylene group having 3 to 6 carbon atoms or —$R^{311a}$—NH—COO—$R^{312a}$—, wherein $R^{311a}$ and $R^{312a}$ are identical or different and represent an alkylene group having 2 to 6 carbon atoms; and $R^{31b}$ represents an alkyl group or aryl group, or (B1) $R^1$ is a group derived from a 4- to 8-membered ring having a group represented by —S—S— in a structure of the ring, $R^2$ is a single bond, and $R^3$ is —O⁻.

5. The method according to claim 1, wherein n is 3 to 30.

6. The method according to claim 1, wherein $Z^1$ is —O—.

7. The method according to claim 1, wherein the polynucleotide is at least one selected from the group consisting of antisense polynucleotides, siRNA, miRNA, miRNA precursors, aptamers, guide RNA, mRNA, noncoding RNA, DNA, and unnatural nucleic acids.

8. The method according to claim 1, wherein a nucleotide length of the polynucleotide is a nucleotide length of not more than 200.

9. The method according to claim 1, wherein the structure represented by general formula (1) is linked to a 5' terminal of the polynucleotide.

10. The method according to claim 1, wherein the composition is a pharmaceutical.

11. The method according to claim 1, wherein the composition is a reagent.

* * * * *

SEQUENCE LISTING

<160> NUMBER OF SEQ ID NOS: 5

<210> SEQ ID NO 1
<211> LENGTH: 19
<212> TYPE: DNA
<213> ORGANISM: Artificial Sequence
<220> FEATURE:
<223> OTHER INFORMATION: 5DTT-DNA sequence

<400> SEQUENCE: 1
aaccgcttcc ccgacttcc                                                19

<210> SEQ ID NO 2
<211> LENGTH: 19
<212> TYPE: DNA
<213> ORGANISM: Artificial Sequence
<220> FEATURE:
<223> OTHER INFORMATION: R-DNA sequence

<400> SEQUENCE: 2
acacgtcctc tcagccctc                                                19

<210> SEQ ID NO 3
<211> LENGTH: 19
<212> TYPE: DNA
<213> ORGANISM: Artificial Sequence
<220> FEATURE:
<223> OTHER INFORMATION: Luciferase antisense polynucleotide

<400> SEQUENCE: 3
cggtatccag atccacaac                                                19

<210> SEQ ID NO 4
<211> LENGTH: 23
<212> TYPE: DNA
<213> ORGANISM: Artificial Sequence
<220> FEATURE:
<223> OTHER INFORMATION: Guide strand RNA sequence

<400> SEQUENCE: 4
uuucgaagua cucagcguaa guu                                           23

<210> SEQ ID NO 5
<211> LENGTH: 23
<212> TYPE: DNA
<213> ORGANISM: Artificial Sequence
<220> FEATURE:
<223> OTHER INFORMATION: Passenger strand RNA sequence

<400> SEQUENCE: 5
cuuacgcuga guacuucgaa auu                                           23